United States Patent [19]

Minagawa et al.

[11] 4,293,472

[45] Oct. 6, 1981

[54] STABILIZED SYNTHETIC RESIN COMPOSITION

[76] Inventors: Motonobu Minagawa, 1-207-3 Shichizacho, Koshigaya; Yutaka Nakahara, 406-71 Minimishimoarai, Iwatsuki; Tohru Haruna, 969-4 Shimohideya, Okegawa, all of Japan

[21] Appl. No.: 33,024

[22] Filed: Apr. 24, 1979

[30] Foreign Application Priority Data

Apr. 24, 1978 [JP] Japan .................................. 53-48599

[51] Int. Cl.³ .......................... C08K 5/36; C07C 65/04
[52] U.S. Cl. ................................ 260/23 XA; 252/404; 560/152
[58] Field of Search .................... 260/45.85 H, 23 XA; 560/152

[56] References Cited

U.S. PATENT DOCUMENTS 3,923,735 12/1975 Schlicting et al. ......... 260/45.9 NC
4,093,591 6/1978 Kline ........................... 260/45.85 H
4,134,879 1/1979 Schmidt ....................... 260/45.85 P
4,171,298 10/1979 Minagawa et al. ................. 560/152

*Primary Examiner*—V. P. Hoke
*Attorney, Agent, or Firm*—Otto S. Kauder

[57] ABSTRACT

New ortho-alkylhydroxybenzyl substituted propanediol compounds of carboxylic acids, aldehydes, ketones, phosphites, phosphates, and phosphonates are disclosed. The propanediol compounds have in the molecule from one to four preferably from one to three ortho-alkylhydroxybenzylpropanediol units, each of which carries one to two ortho-alkylhydroxybenzyl groups, and are highly effective stabilizers for a variety of synthetic resins.

Stabilizer compositions comprising a orthoalkylhydroxybenzylpropanediol compound and a known polymer stabilizer, as well as synthetic resins stabilized with such stabilizer compositions, are also disclosed.

18 Claims, No Drawings

STABILIZED SYNTHETIC RESIN COMPOSITION

BACKGROUND OF THE INVENTION

This invention relates to a new class of phenolic compound stabilizers for synthetic resins and to synthetic resin stabilizer compositions comprising these phenolic compounds as well as to synthetic resins stabilized with such phenolic compounds and with stabilizer compositions comprising these phenolic compounds along with known polymer stabilizers.

The usefulness of phenols in stabilizer compositions for synthetic resins was recognized early in the development of polymer stabilization by additives, as disclosed for example by F. Duggan in U.S. Pat. No. 2,126,179 of Aug. 9, 1938, W. Leistner in U.S. Pat. No. 2,564,646 of Aug. 14, 1951, and W. Fischer in U.S. Pat. No. 2,625,521 of Jan. 13, 1953, in the stabilization of polyvinyl chloride resin compositions. Over the years, phenolic stabilizers have been used in an expanding variety of synthetic resins and an enormous number of disclosures of new phenolic stabilizers has accumulated. Rather than attempt to list every one of these disclosures, A. DiBattista in U.S. Pat. No. 3,824,192 of July 16, 1974 and M. Minagawa in U.S. Pat. No. 3,849,370 of Nov. 19, 1974 and in U.S. Pat. No. 3,869,423 of Mar. 4, 1975 are cited as summaries of a very large part of the existing art of phenolic stabilizers. In particular, DiBattista at Column 6 Line 48 to Column 10 Line 49 includes twelve classes of phenols and over eightly individual members thereof.

More recently, J. Song in U.S. Pat. No. 3,795,700 of Mar. 5, 1974 disclosed 4 alkyl-2,6-dimethyl-3-hydroxybenzyl esters of carboxylic acids having the formula:

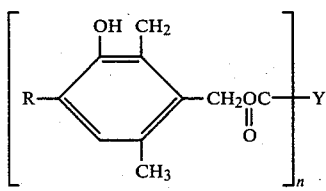

wherein R is branched chain alkyl group containing three to about twelve carbon atoms; Y is the residue of the carboxylic acid Y(COOH)$_n$, provided that when Y is alkyl and n is one, Y contains more than ten carbon atoms; and n is one to four.

I. Hechenbeikner in U.S. Pat. No. 3,839,506 of Oct. 1, 1974 disclosed hindered phenolic phosphonate esters having the formula:

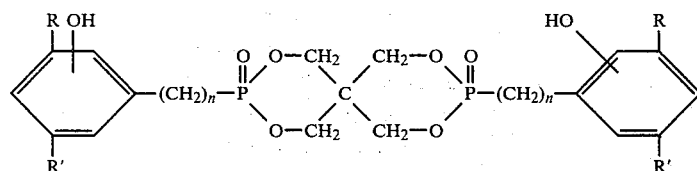

where n is an integer of 1 to 4, R is alkyl, hydrogen, cycloalkyl or aralkyl and R' is alkyl, cycloalkyl or aralkyl.

E. Kleiner in U.S. Pat. No. 3,944,594 of Mar. 16, 1976 disclosed hindered phenolic esters having the formula:

wherein
 X is oxygen or sulfur
 a is an integer from 2 to 6,
 b is an integer from 3 to 40, and
 R is

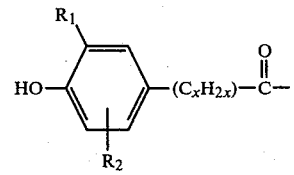

wherein
 R$_1$ is an alkyl group from 1 to 8 carbon atoms,
 R$_2$ is hydrogen or an alkyl group from 1 to 8 carbon atoms, and
 x is an integer from 0 to 6.

Phenolic stabilizers are also employed in conjunction with other stabilizers such as esters of thiodipropionic acid or organic phosphites in the stabilization of polypropylene and other synthetic resins against degradation upon heating or ageing under atmospheric conditions. Disclosures by C. Tholstrup, U.S. Pat. Nos. 3,033,814 of May 8, 1962 and 3,160,680 of Dec. 8, 1964; L. Rayner, U.S. Pat. No. 3,181,971 of May 4, 1965; D. Brown, U.S. Pat. No. 3,242,135 of Mar. 22, 1966; S. Murdock, U.S. Pat. No. 3,245,949 of Apr. 12, 1966; H. Hagemeyer, U.S. Pat. No. 3,282,890 of Nov. 1, 1966; J. Casey, U.S. Pat. Nos. 3,496,128 of Feb. 17, 1970 and 3,586,657 of June 22, 1971; M. Minagawa, U.S. Pat. Nos. 3,549,572 of Dec. 22, 1970, and 3,629,189 of Dec. 21, 1971, and 3,673,152 of June 27, 1972, 3,849,370 of Nov. 19, 1974 and 3,869,423 of Mar. 4, 1975; W. Drake U.S. Pat. No. 3,624,026 of Nov. 30, 1971; A. DiBattista, U.S. Pat. No. 3,824,192 of July 16, 1974; B. Cook, U.S. Pat. No. 3,850,877 and H. Mueller U.S. Pat. No. 3,850,918 of Nov. 26, 1974; M. Dexter U.S. Pat. Nos. 3,856,748 of Dec. 24, 1974, and 3,888,824 of June 10, 1975, and 3,903,160 of Sept. 2, 1975; P. Klemchuk U.S. Pat. No. 3,860,558 of Jan. 14, 1975; M. Rasberger U.S. Pat. Nos. 3,867,340 of Feb. 18, 1975 and 3,901,931 of Aug. 26, 1975; H. Brunetti U.S. Pat. Nos. 3,867,337 of Feb. 18, 1975 and 3,873,498 of Mar. 25, 1975; S. Rosenberger U.S. Pat. Nos. 3,884,874 of May 20, 1975 and 3,887,518 of June 3, 1975; C. Ramey U.S. Pat. No. 3,907,803 of Sept. 23, 1975 are representative of a very large number of stabilizer combinations including dilau-

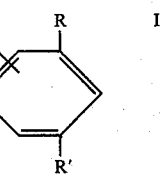

I ryl and distearyl thiodipropionate or other dialkyl thiodipropionates along with polyhydric phenols and sometimes organic phosphites, metallic stearates, ultraviolet absorbers, nickel compounds, and heavy metal deactivators for use in polypropylene and other polyolefins.

Disclosures by R. Werkheiser, U.S. Pat. No. 2,726,226 of Dec. 6, 1975; I. Salyer et al, U.S. Pat. No. 2,985,617 of May 23, 1961; L. Friedman, U.S. Pat. No. 3,039,993 of June 19, 1962; W. Nudenberg, U.S. Pat. No. 3,080,338 of Mar. 5, 1963; C. Fuchsman, U.S. Pat. No. 3,082,187 of Mar. 19, 1963; H. Orloff et al, U.S. Pat. No. 3,115,465 of Dec. 24, 1963; A. Nickolson, U.S. Pat. No. 3,167,526 of Jan. 26, 1965; A. Hecker et al, U.S. Pat. Nos. 3,149,093 of Sept. 15, 1964, 3,244,650 of Apr. 5, 1966 and 3,225,136 and 3,255,151 of June 7, 1966; C. Bawn, U.S. Pat. No. 3,352,820 of Nov. 14, 1967; D. Miller, U.S. Pat. No. 3,535,277 of Oct. 20, 1970; J. Casey, U.S. Pat. No. 3,586,657 of June 22, 1971; C. Abramoff U.S. Pat. No. 3,856,728 of Dec. 24, 1974; M. Minagawa, U.S. Pat. Nos. 3,869,423 of Mar. 4, 1975 and 3,907,517 of Sept. 23, 1975; and British Pat. Nos. 846,684, 851,670, and 866,883 are representative of stabilizer combinations including organic phosphites, polyhydric phenols, and other active ingredients.

As summarized in a publication by D. Plank and J. Floyd (title—"Polycarbonates: A New Concept in Stabilization for Polypropylene", meeting preprints, Society of Plastics Engineers, Houston, Texas, April 1975; pages 33–37), there have long been several problems with using phenols as stabilizers despite their widespread use. Many phenol stabilizers are volatilized out of the polymer at high use temperatures. Some phenol stabilizers are extractable under certain use conditions. The oxidative products of most phenols are highly colored, thus imparting a yellow color to the polymer. Many phenols are reactive towards acidic or basic residues in the polymer. Following are disclosures of suggested ways to overcome these problems.

L. Friedman has disclosed in U.S. Pat. No. 3,053,878 of Sept. 11, 1962 a class of linear phosphite polymers having the formula

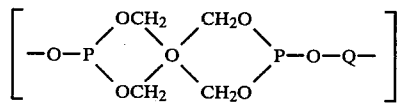

in which Q is the alkylene or arylene portion of a dihydric alcohol or dihydric phenol. R. Morris et al. in U.S. Pat. No. 3,112,286 of Nov. 26, 1963 disclosed phosphites having the formula

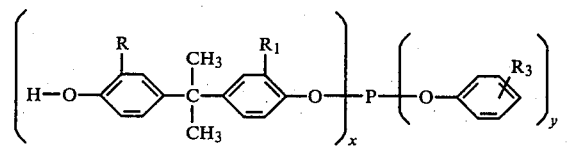

in which R represents a bulky hydrocarbon group such as t-butyl, t-amyl, t-hexyl, cyclohexyl, t-pentyl, t-octyl, phenyl, and the like: $R_1$ represents hydrogen and R; $R_3$ represents an alkyl group from 6 to 20 carbon atoms which is preferably in the meta or para position; x represents a number of from 1 to 3 inclusive; y represents a number of from 0 to 2 inclusive and the sum of the numerical value of x+y is always exactly 3.

D. Brown, U.S. Pat. No. 3,297,631 of Jan. 10, 1967 disclosed condensation products of phosphorus compounds with bisphenols and trisphenols which may be represented by the structures:

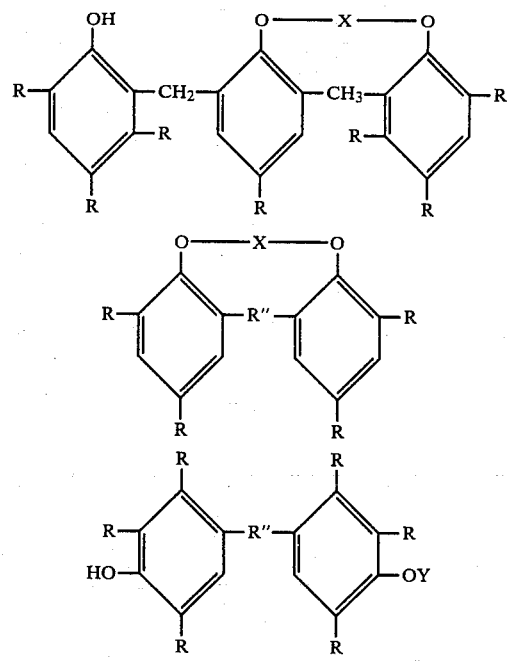

where:

X is selected from the following: $>$P—OR'; $>$P—R';

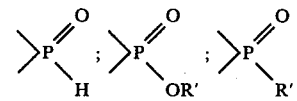

and Y is selected from the following: —P(OR')$_2$;

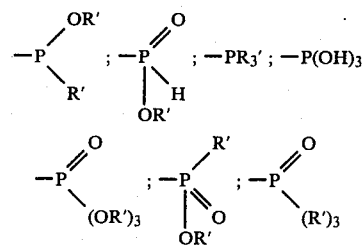

R is hydrogen, alkyl of 1 to 16 carbon atoms or aryl or a combination of these; R' is alkyl of 1 to 16 carbon atoms or aryl, anf R" is alkylidene of 1 to 16 carbon atoms or an aryl-substituted alkylidene.

C. Baranauckas, U.S. Pat. No. 3,305,608 of Feb. 21, 1967, disclosed phenolic phosphites useful as polymer stabilizers prepared by reacting a triorganophosphite, a polyol, and an aromatic material having two to six phenolic hydroxyl groups at 60°–180° C. in specified proportions.

G. Brindell, U.S. Pat. No. 3,412,064 of Nov. 19, 1968 disclosed phenolic phosphites represented by the general formula:

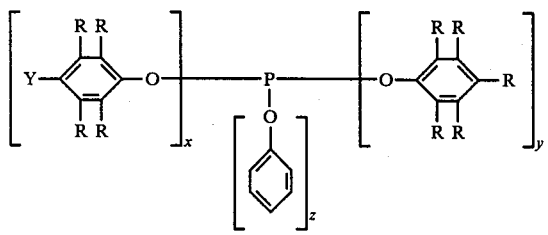

where x is from 1 to 3, y and z each from 0 to 2, x+y+z=3, R is hydrogen or alkyl and Y is hydroxyl or a group of the formula

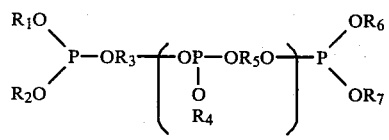

where R is hydrogen or alkyl.

M. Larrison, U.S. Pat. No. 3,419,524 of Dec. 31, 1968, disclosed phosphites useful as polymer stabilizers having the formula:

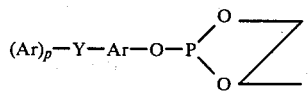

where $R_1$, $R_2$, $R_4$, $R_6$, and $R_7$ are aryl or haloaryl, and $R_3$ and $R_5$ area polyalkylidene glycol or an alkylidene bisphenol or a hydrogenated alkylidene bisphenol or a ring halogenated alkylidene bisphenol from which the two terminal hydrogens have been removed. O. Kauder et al, U.S. Pat. Nos. 3,476,699 of Nov. 4, 1969 and 3,655,832 of Apr. 11, 1972 disclosed organic phosphites containing a free phenolic hydroxyl group and defined by the formula:

$$(Ar)_p-Y-Ar-O-P\begin{matrix}O\\ \\O\end{matrix}Z$$

wherein Z is selected from the group consisting of hydrogen and aliphatic, cycloaliphatic, aromatic, heterocyclic and $(Ar)_p$—Y—Ar groups, taken in sufficient number to satisfy the valences of the two phosphite oxygen atoms; Y is a polyvalent linking group selected from the group consisting of oxygen; aliphatic, cycloaliphatic and aromatic hydrocarbon groups attached to each Ar group through a carbon atom not a member of an aromatic ring; oxyaliphatic, thioaliphatic, oxycycloaliphatic, thiocycloaliphatic; heterocyclic; oxyheterocyclic, thioheterocyclic, carbonyl, sulfinyl; and sulfonyl groups; Ar is a phenolic nucleus which can be phenyl or a polycarbocyclic group having condensed or separate phenyl rings; each Ar group is either connected through an oxygen atom to a phosphite group or contains a free phenolic hydroxyl group, or both; and p is a number, one or greater, and preferably from one to four, which defines the number of Ar groups linked to Y.

L. Friedman, U.S. Pat. No. 3,516,963 of June 23, 1970, disclosed phosphites having the formula:

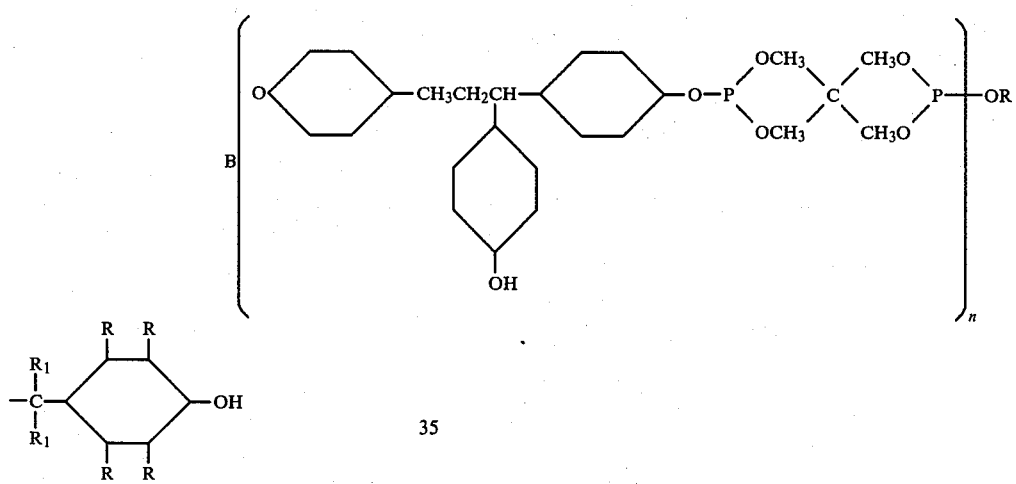

where R is alkyl, alkenyl, aryl, aralkyl, haloaryl, haloalkyl or

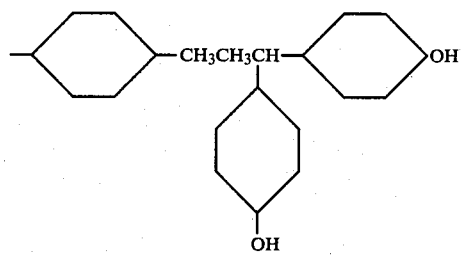

and n is an integer of at least 1. n can be 2, 3, 4, 5, 6, 7, 8, 10, 50, 100 or even more.

D. Bown et al. in U.S. Pat. Nos. 3,510,507 of May 5, 1970 and 3,691,132 of Sept. 12, 1972 disclosed polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula,

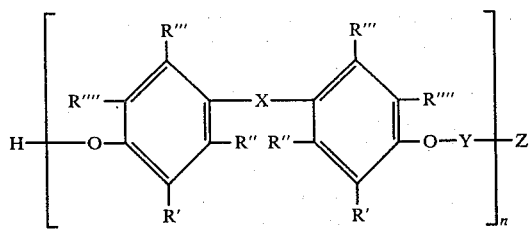

where X is selected from the group consisting of

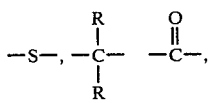

—C—C, and C—A—C— where A is a $C_1$ to $C_{16}$ alkylene or an arylene; R',R'', R''', and R'''' are selected from the group consisting of hydrogen, $C_1$ to $C_{18}$ alkyls, and an aryl group; Y is selected from the group of

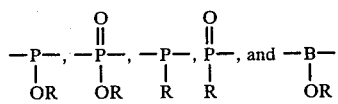

where R is hydrogen, a $C_1$ to $C_{18}$ alkyl, or aryl;

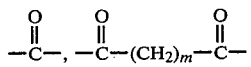

where m is 0 to 10, preferably 4 to 8,

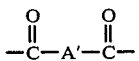

where A' is $(CH_2)_n$—S—$(CH_2)_n$ or —$(CH_2)_n$—S—$(CH_2)_m$—S—$(CH_2)_n$ where n is 0 to 10, preferably 2 and m is 0 to 10, preferably 5;

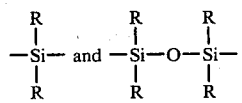

where R is an alkyl, preferably methyl, and Z is

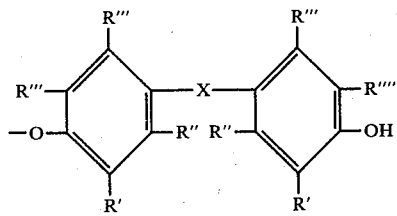

where R', R'', R''', R'''', and X correspond respectively to the R', R'', R''', R'''', and X previously selected when n has a value from 1 to 15, or Z may be derived from the compound used to introduce Y into the product when n has a value from 2 to 15, for example —R or —OR where R is hydrogen, an alkyl, or aryl. When Y in the formula of Brown's stabilizer is

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto)paraxylylene, and 10,24-dithiotetracontane.

SUMMARY OF THE INVENTION

In accordance with this invention, there are prepared 2-orthoalkylhydroxybenzyl substituted propane-1,3-diol compounds having the formula:

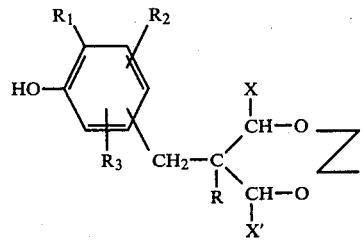

in which $R_1$ is an alkyl group having 1 to 8 carbon atoms, $R_2$ and $R_3$ are hydrogen or alkyl groups having 1 to 8 carbon atoms, R is hydrogen, an alkyl group having 1 to 8 carbon atoms, an alkenyl group having 2 to 8 carbon atoms, or an ortho-alkylhydroxybenzyl group

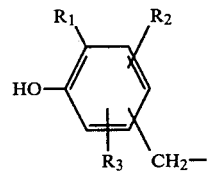

X and X' are each independently hydrogen, alkyl groups, aryl groups, aralkyl groups, or alkaryl groups having 1 to 18 carbon atoms, provided that X and X' are not simultaneously hydrogen; and Z is selected from the group consisting of acyl groups, alkylidene groups, cycloalkylidene groups, singly linked phosphorus ester groups and doubly linked phosphorus ester groups taken in sufficient number to satisfy the valences of the two propanediol oxygen atoms; the acyl groups Z having the formula R'CO— in which R' is —$CH_2CH_2$—S—$R_9$ or

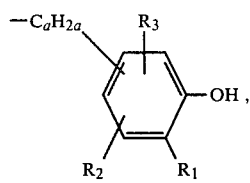

$R_9$ is an alkyl group having 1 to 30 carbon atoms, and a is 0, 1, or 2;

the alkylidene groups Z having the formula:

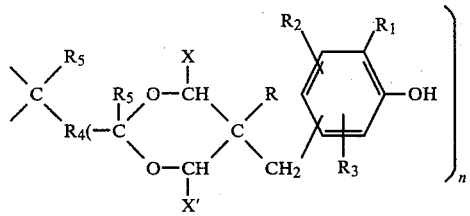

in which n is 0 or 1; when n is 0 $R_4$ is hydrogen, alkyl having 1 to 8 carbon atoms, alkenyl having 2 to 8 carbon atoms, mononuclear aryl, mononuclear alkaryl, mononuclear aralkyl, or hydroxyl-substitution products thereof, and when n is 1 $R_4$ is a single bond, an alkylene group having 1 to 8 carbon atoms, a mononuclear arylene group, a mononuclear arylalkylene group, a mononuclear alkylarylene group, or hydroxyl-substitution products thereof; and $R_5$ is hydrogen, alkyl having 1 to 8 carbon atoms, or

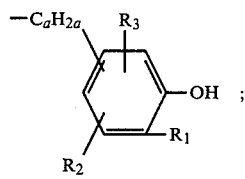

the cycloalkylidene groups having the formula:

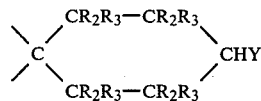

in which Y is hydrogen or

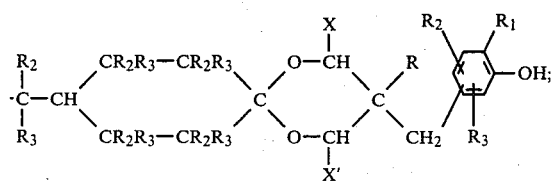

the singly linked phosphorus ester Z groups having the formula

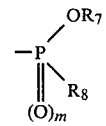

in which m is 0 or 1; $R_7$ is the residue obtained by reaction of one hydroxyl group of an aliphatic or aromatic compound having 1 to 40 carbon atoms, and 1 to 4 hydroxyl groups; $R_8$ is —O—$R_7$, alkyl having 1 to 8 carbon atoms, phenyl, benzyl, or

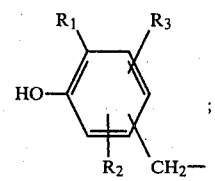

and the doubly linked phosphorus ester Z groups having the formula

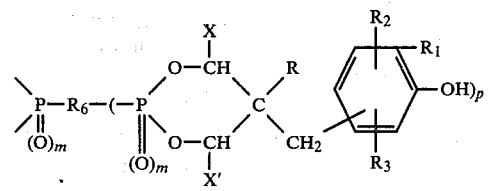

in which m is 0 or 1 and p is 0, 1, 2, or 3; when p is 0 $R_6$ is alkyl, phenyl, benzyl,

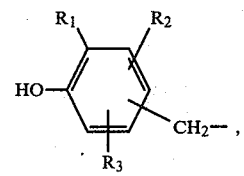

or a residue linked through one oxygen of a monohydric, dihydric, trihydric, or tetrahydric alcohol or phenol having 1 to 40 carbon atoms; and when p is 1, 2, or 3 $R_6$ is a residue linked through two oxygens of a dihydric, trihydric, or tetrahydric alcohol or phenol having 2 to 40 carbon atoms.

The ortho-alkylhydroxybenzylpropanediol compounds are highly effective stabilizers for a variety of synthetic resins. Stabilizer compositions for synthetic resins comprise an ortho-alkylhydroxybenzylpropanediol compound along with at least one known polymer stabilizer in proportions to each other that can range from about 20 to 1 to about 1 to 20 by weight.

DESCRIPTION OF THE PREFERRED EMBODIMENTS

Throughout this specification, the terms "propanediol" or "propanediol compound" are used as brief representations of the 2-ortho-alkylhydroxybenzyl substituted propane diol compounds defined in this invention. Throughout the structural formulas, the symbol X as a substituent on a benzene ring indicates a tertiary butyl group.

In the propanediol compounds of this invention, there is present at least one ortho-alkylhydroxybenzyl group at the 2-position of the substituted 1,3-propanediol structure, and at least one alkyl, aryl, alkaryl, or aralkyl group at the 1-position or the 3-position of the substituted propanediol structure. A second ortho-alkylhydroxybenzyl group can also be present at the same 2-position, and the multifunctional Z groups can link together up to 4 other-alkylhydroxybenzyl-propanediol substructures of which each carries one ortho-alkylhydroxybenzyl group at the 2-position and can also carry a second such group. Accordingly, there can be present as many as eight ortho-alkylhydroxybenzyl groups in the propanediol compounds of this invention. When more than one ortho-alkylhydroxybenzyl group is present, the groups can be identical or different.

$R_1$, the required ortho-alkyl substituent in each ortho-alkylhydroxybenzyl group, as well as $R_2$, $R_3$, and R when these substituents are alkyl, has from 1 to 8 carbon atoms and can be, for example, methyl, ethyl, n-propyl, isopropyl, t-butyl, sec-butyl, isobutyl, n-amyl, sec-amyl, t-amyl, neopentyl, 4-methyl-2-pentyl, 2-ethylbutyl, hexyl, sec-hexyl, n-heptyl, 2-heptyl, 4-heptyl, n-octyl, 2-ethylhexyl, 2-ethyl-4-methylpentyl, and 2-octyl. The relative orientation of the phenolic hydroxyl group to the benzyl side chain is not critical and can be ortho, meta, and para. Thus, useful ortho-alkylhydroxybenzyl groups that can be present in the propanediol compounds of this invention include 2-hydroxy-3,5-dimethylbenzyl, 2-hydroxy-3-t-butyl-6-t-octylbenzyl, 2,4,6-tri-t-butyl-3-hydroxybenzyl,2,6-diethyl-4-t-butyl-3-hydroxybenzyl, 3-isopropyl-4-hydroxybenzyl,3-methyl-5-t-butyl-4-hydroxybenzyl, and 2,3,5-trimethyl-4-hydroxybenzyl.

The second substituent at the 2-position of the propanediol compound, the group R, can be alkyl of 1 to 8 carbon atoms, ortho-alkylhydroxybenzyl, hydrogen, or an alkenyl group of 2 to 8 carbon atoms. Useful alkenyl groups, for example, are vinyl, 1-propenyl, allyl, methallyl, crotyl, 3-buten-1-yl, 2-methyl-2-buten-1-yl, and 4-octen-1-yl.

The structure Z in the propanediol compound is linked to the 1- and 3-positions of the ortho-alkylhydroxybenzylpropanediol group, and is made up of as many groups as required to satisf these two positions linkages. Accordingly, when Z is acyl, there are two acyl groups R'CO—, which can be the same or different and the propanediol compound has the formula:

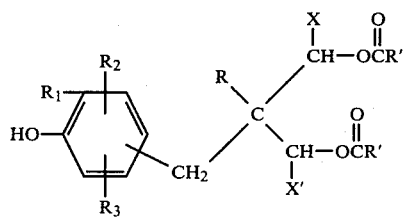

In the formula R' has the structure —CH$_2$CH$_2$SR$_9$ or

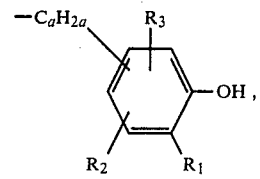

in which $R_9$ is an alkyl group having 1 to 30 carbon atoms, a is 0, 1, or 2, and X, X', $R_1$, $R_2$, and $R_3$ are as defined above. $R_9$ alkyl groups can be those disclosed for $R_1$ as well as such higher alkyls as 1-nonyl, 3,5,5-trimethylhexyl, n-decyl, isodecyl, n-dodecyl, 2-butyloctyl, tetradecyl, hexadecyl, 2-hexyldecyl, n-octadecyl, eicosanyl, tetracosanyl, and triacontanyl.

When Z is alkylidene or cycloalkylidene, one Z group is linked to both the 1- and 3-positions of an ortho-alkylhydroxybenzylpropanediol group thus forming a heterocyclic ring of the carbonyl carbon atom with the two oxygens and three carbons of the propanediol. The alkylidene Z group has the formula:

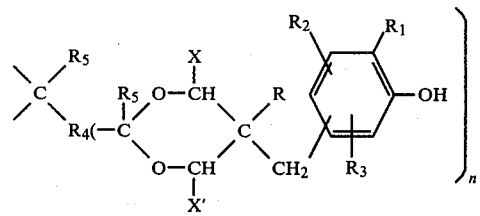

and the propanediol compound containing the alkylidene Z group has the formula

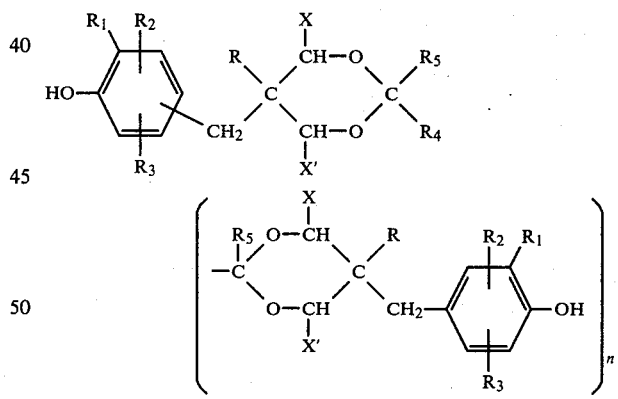

in which R, $R_1$, $R_2$, and $R_3$ are as already defined, and n is zero or one. When n is 0, $R_4$ is a one-valent structure such as hydrogen, alkyl having 1 to 8 carbon atoms, alkenyl having 2 to 8 carbon atoms, a mononuclear aromatic group which can be aryl, alkaryl, aralkyl, or phenolic hydroxyl substitution products of these groups. When n is 1, $R_4$ is a two-valent structure such as a single bond, an alkylene group having 1 to 8 carbon atoms, or a bifunctional mononuclear aromatic group which can be arylene, alkylarylene, arylalkylene, or such groups substituted with phenolic hydroxyl groups.

$R_5$ is also a one-valent structure and can be hydrogen, alkyl having 1 to 8 carbon atoms, or the structure

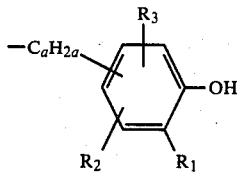

R₄ and R₅ can be the same or different. Accordingly, R₄ for example can be, besides hydrogen and aliphatic groups already recited, phenyl, 3,4-dimethylphenyl, 2-phenethyl, p-t-butylphenyl, 2-hydroxyphenyl, 3-methyl-5-t-butyl-4-hydroxyphenyl, 2(3',5'-di-t-butyl-4'-hydroxyphenyl)ethyl, ethylene, 1,4-butylene, 3-methyl-1,5-pentylene, 1,4-phenylene, 2,6-dimethyl-1,3-phenylene, 1,4-xylene, and p-phenyleneethylene. By suitable selection of R₄ and R₅ there result alkylidene groups such as ethylidene, 1,1-propylidene, 2,2-propylidene, isobutylidene, n-butylidene, 2-ethyl-1,1-hexylidene, acrylidene, crotylidene, benzylidene, 3-methylbenzylidene, salicylidene, 1-phenyl-1,1-propylidene and 1-(p-hydroxyphenyl)-1,1-ethylidene.

Cycloalkylidene Z groups have the formula

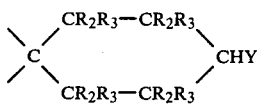

in which independently at each occurrence R₂ and R₃ are as defined above and Y is hydrogen or the structure

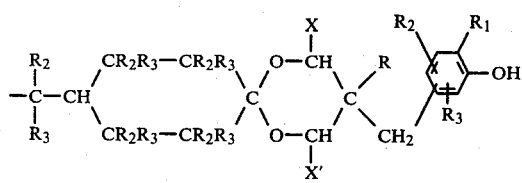

Thus suitable cycloalkylidene groups include cyclohexylidene, 2-methylcyclohexylidene, 3,3,5-trimethylcyclohexylidene, and the 2,2-propanedicyclohexylidene group

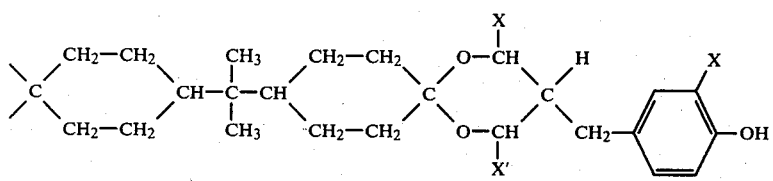

derived from 4,4'-isopropylidenedicyclohexanone and a substituted 2(3'-t-butyl-4'-hydroxybenzyl)-1,3-propanediol.

Phosphorus ester Z groups can be linked to the orthoalkylhydroxybenzylpropanediol group of the propanediol compound in such a way that there are two singly linked phosphorus ester groups, each linked to one oxygen of the propanediol compound in an open chain configuration. The two singly linked phosphorus ester groups in the propanediol compound of this invention can be the same or different.

The singly linked phosphorus ester groups has the formula

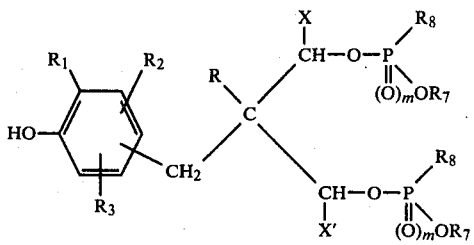

and the propanediol compound according to the invention in which Z is a singly linked phosphorus ester group can be represented by the formula

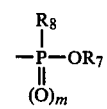

in which m is zero or one, R is derived from an alcohol or phenol and accordingly is an aliphatic or aromatic group having 1 to 40 carbon atoms and from zero to 3 free alcoholic or phenolic hydroxyl groups, and R₈ is alkyl having 1 to 8 carbon atoms, phenyl, benzyl, ortho-alkylhydroxybenzyl having the structure

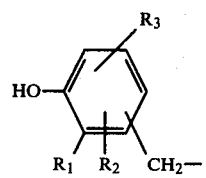

in which R₁, R₂, and R₃ are as previously defined, or a second —OR₇ group; when there are two —OR₇ groups they can be the same or different.

R₇ aliphatic groups include alkyl groups of the kind defined earlier for R₁ and R₉ and higher homologs thereof up to 40 carbon atoms; alkenyl groups such as those defined earlier for R and higher homologs such as 10-undecenyl, palmitoleyl, and linoleyl; and hydroxyl substituted aliphatic groups such as 2-hydroxyethyl, 12-hydroxystearyl, and ricinoleyl. R₇ aromatic groups have a minimum of 6 carbon atoms and preferably non-condensed aromatic rings that can be substituted with alkyl groups and phenolic hydroxyl groups. Useful R₇ aromatic groups include phenyl, o-tolyl, p-t-butylphenyl. 2,3,5-trimethylphenyl, p-dodecylphenyl, benzyl, p-dodecylbenzyl, beta-(3,5-di-t-butyl-4-hydroxyphenyl)propyl, 2,5-di-t-butyl-4-hydroxyphenyl, and polycyclic polyhydric phenol groups in which one phenolic group is linked to the phosphorus ester and the remaining one to three phenolic hydroxyl groups are free, as for example polycyclic polyhydric phenol groups of bisphenol A, 2,2-di(p-hydroxyphenyl)octane, 1,1,2,2-tetrakis-(p-hydroxyphenyl)ethylene, 4,4'-cyclohexylidenebisphenol and ortho-substituted derivatives thereof such as 2,2'-methylene bis(4-methyl-6-t-butyl-phenol), 2,2'-methylene bis(4-ethyl-6-t-butyl-phenol), 2,2'-methylene bis(4-methyl-6-(1-methylcyclohexyl)phenol), 2,2'-n-butylidene bis(4,6-dimethylphenol), bis-1,1-(2'-hydroxy-3'5'-dimethylphenyl)-3,5,5-trimethylhexane, 2,2'-cyclohexylidene bis(4-ethyl-6-t-butyl-phenol), 4,4'-bis(2,6-di-t-butylphenol), 4,4'-methylene bis(2,6-di-t-butylphenol), 4,4'-isopropylidene bis(2-phenylethylphenol), 4,4'-n-butylidene bis(3-methyl-6-t-butylphenol), 4,4'-cyclohexylidene bis (2-t-butylphenol), 4,4'-cyclohexylidene bis(2-cyclohexylphenol), and 4,4'-benzylidene bis (2-t-butyl-5-methylphenol).

Additional R$_7$ aromatic groups are derived from bisphenols having two ortho-substituted phenolic groups linked through oxygen or sulfur, such as 4,4'-oxobis(3-methyl-6-isopropylphenol), 4,4'-thiobis(2-methyl-6-t-butyl phenol), 4,4'-thiobis(3-methyl-6-t-butylphenol), 4,4'-sulfobis (3-methyl-6-t-butylphenol), bis(2-methyl-4-hydroxy-5-t-butylbenzyl)sulfide, bis(3,5-di-t-butyl-4-hydroxybenzyl)sulfide, 2,2'-thiobis (4-hydroxybenzyl) sulfide, 2,2'-thiobis(4-tObutyl-6-methylphenol), 2,2'-thiobis(4-methyl-6-t-butyl-phenol), and 2,2'-thiobis(4,6-di-t-butylphenol).

R$_7$ aromatic groups also include groups derived from trisphenols such as 1,1,3-tris(2'methyl-4'-hydroxy-5'-t-butylphenyl)butane, 1,3,5-tris(3'-5'-di-t-butyl-4'-hydroxybenzyl)-2,4,6-trimethylbenzene, 2,2-bis(3'-t-butyl-4'-hydroxyphenyl)-4-(3'',5''-di-t-butyl-4''-hydroxyphenyl)butane, and 2,2-bis(2'methyl-5-t-butyl-4'hydroxyphenyl)-4-(3'',5''-di-t-butyl-4''-hydroxyphenyl)butane.

In the formula of the phosphorus ester, when m is zero the ester is an ester of trivalent phosphorus, that is a phosphite ester when R$_8$ is linked to phosphorus through oxygen as in an OR$_7$ group, and a phosphonite ester when R$_8$ is one of the previously defined groups linked to phosphorus through carbon. When m is one, the ester is an ester of pentavalent phosphorus, that is a phosphate ester when R$_8$ is linked to phosphorus through oxygen and a phosphenate ester when R$_8$ is linked to phosphorus through carbon. Accordingly, by suitable assignment of m, R$_7$, and R$_8$, there can result the following examples of singly linked phosphorus ester groups, any two of which taken together can constitute the Z group.

Diethyl phosphite, di-n-butyl phosphite, di-2-ethylhexyl phosphite, di-n-hexadecyl phosphite, ethyl isodecyl phsophite, diphenyl phosphite, di-2,4-di-t-butylphenyl phosphite, 2-ethylhexyl nonylphenyl phosphite, n-dodecyl bisphenol A phosphite, isooctyl 1,1,3-tris(2'-methyl-4'-hydroxy-5'-t-butylphenyl)butane phosphite, dimethyl phosphate, di-n-pentyl phosphate, phenyl tridecyl phosphate, phenyl n-hexanephosphonite, n-octadecyl benzenephosphonite, methyl methanephosphonate, n-propyl benzylphosphonate, and 2,4-dimethylphenyl P-3,5-di-t-butyl-4-hydroxybenzylphosphonate.

Phosphorus ester Z groups can also be linked to the orthoalkylhydroxybenzylpropanediol group of the propanediol compound of the invention in such a way that one phosphorus ester group bridges both oxygens of the propanediol compound, thereby forming a six-membered ring system of three carbon atoms, two oxygen atoms and the phosphorus ester group phosphorus atom. Such a doubly linked phosphorus ester Z group has the formula

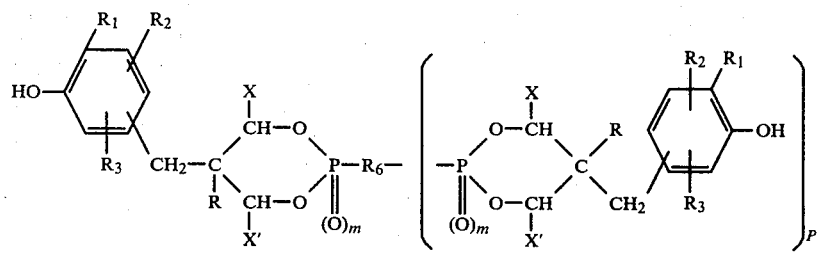

and a propanediol compound according to the invention in which Z is such a doubly linked phosphorus ester group can be represented by the formula

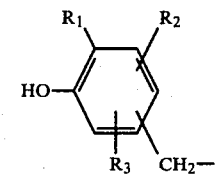

In each of these formulas, R$_1$, R$_2$, R$_3$, and R are as previously defined, m is 0 or 1 and p is 0, 1, 2, or 3. When p is zero, R$_6$ is alkyl, phenyl, benzyl, or an aliphatic or aromatic group linked to phosphorus through oxygen having, like R$_7$ defined above, 1 to 40 carbon atoms and from zero to 3 free alcoholic or phenolic hydroxyl groups. When p is 1,2, and 3, R$_6$ is a multivalent group linking together two or more phosphorus ester groups through an oxygen atom of each phosphorus ester group linked by R$_6$. Accordingly, R$_6$ is a residue of a dihydric alcohol having 2 to 40 carbon atoms, a trihydric alcohol having 3 to 40 carbon atoms, a tetrahydric alcohol having 4 to 40 carbon atoms, or a dihydric, trihydric, or tetrahydric phenol having 6 to 40 carbon atoms. Suitable R$_6$ groups include, therefore, all the alkyl groups earlier defined for R$_1$ and all the oxyaliphatic and oxyaromatic groups earlier defined for R$_7$. Multivalent R$_6$ groups include such doubly linked groups as ethylene-1,2-dioxy, 2,2-dimethylpropane-1,3-dioxy, n-octadecane-1,12-dioxy, and multiply linked polyoxyaromatic groups derived from each of the polyhydric phenols earlier recited as a source of aromatic $R_7$ groups.

By suitable assignment of m, p, and $R_6$, there can result the following examples of doubly linked phosphorus ester Z groups that join in a six member ring with the two oxygens of the propanediol compound of the invention:

n-Butyl cyclic phosphite, 2-ethylhexyl cyclic phosphite, phenyl cyclic phosphite, 6-hydroxyhexyl cyclic phosphite, 2,5-dimethyl-1,4-phenylenebis (cyclic phosphite), methyl cyclic phosphate, benzyl cyclic phosphate, bisphenol A cyclic phosphate, 4,4′-isopropylidenebisphenyl(cyclic phosphate), cyclic ethanephosphonite, cyclic benzenephosphonite, cyclic n-butanephosphonate, and cyclic 4-t-butyl-2,6-dimethyl-3-hydroxybenzylphosphonate.

The substituted 2-orthoalkylhydroxybenzylpropane-1,3-diol compounds of the invention are prepared by a condensation reaction of a substituted 2-orthoalkylhydroxybenzyl-propane-1,3-diol with a condensing agent that introduces the Z group into the molecule. When the Z group comprises acyl groups R'—CO—, the condensing agent is an acylating agent which can be a carboxylic acid, R'COOH, acid halide, R'COHal, anhydride R'CO—O—COR', or conveniently displaced carboxylic ester R'CO—OR" where R" is, for example, methyl, ethyl, or phenyl, and R' is as previously defined. The reaction of a substituted 2-ortho-alkylhydroxybenzylpropane-1,3-diol with an acylating agent can be represented by equations as in scheme 1.

SCHEME 1

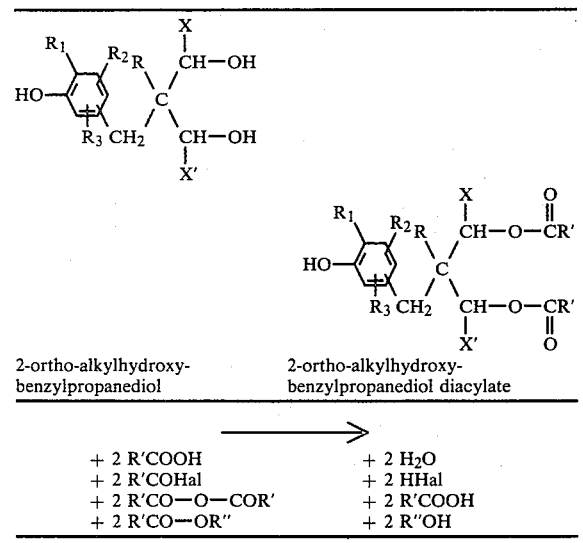

2-ortho-alkylhydroxy-benzylpropanediol → 2-ortho-alkylhydroxy-benzylpropanediol diacylate

| + 2 R'COOH | + 2 H₂O |
| + 2 R'COHal | + 2 HHal |
| + 2 R'CO—O—COR' | + 2 R'COOH |
| + 2 R'CO—OR" | + 2 R"OH |

Preferred process conditions for the condensation reactions with acylating condensing agents as shown in Scheme 1 are as follows. Carboxylic acid R'COOH condensing agents are suitably heated with the desired 2-ortho-alkylhydroxybenzylpropanediol at 50° to 220° C., a catalyst being used if desired that can be a strong acid, a base, or a heavy metal compound. Examples of catalysts in each category are trifluoromethanesulfonic acid, potassium aluminate; and di-n-octyltin oxide. Water of reaction can be removed to displace the reaction equilibrium in the desired direction by application of vacuum or the use of an entraining solvent such as heptane or toluene. Carboxylic acid halide R'COHal condensing agents are suitably brought into reaction with the desired 2-ortho-alkylhydroxybenzyl-propanediol in the temperature range of −20° to 150° C. The by-product hydrogen halide can be allowed to escape or to react with an acid acceptor such as pyridine, triethylamine, or aqueous alkali.

Carboxylic acid anhydride R'CO—O—COR' condensing agents are suitably heated with the desired 2-ortho-alkylhydroxybenzylpropanediol at 30° to 160° C., with or without catalyst or solvent as desired. Acids, bases, and heavy metal compounds all possess catalytic activity for this reaction.

Carboxylic acid ester R'CO—OR" condensing agents are suitably heated with the desired 2-ortho-alkylhydroxybenzylpropanediol at 80° to 220° C., preferably with use of a catalyst or the acid, base, or heavy metal compound type, and intermittent or continuous removal of the by-product lower alcohol or phenol by distillation.

When the Z group comprises an alkylidene group

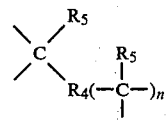

the condensing agent is a carbonyl compound derivative which can be a carbonyl compound (ketone or aldehyde) of the formula $O{:}C(R_5)$—$R_4$—$(CR_5{:}O)_n$ in which $R_4$, $R_5$, and n are as previously defined or a conveniently displaced ketal or acetal thereof which can be open chain or cyclic, for example a dimethyl ketal or a propylene glycol cyclic ketal. The reaction of a 2-ortho-alkylhydroxybenzylpropane-1,3-diol with a carbonyl compound derivative can be represented by equations as in Scheme 2.

SCHEME 2

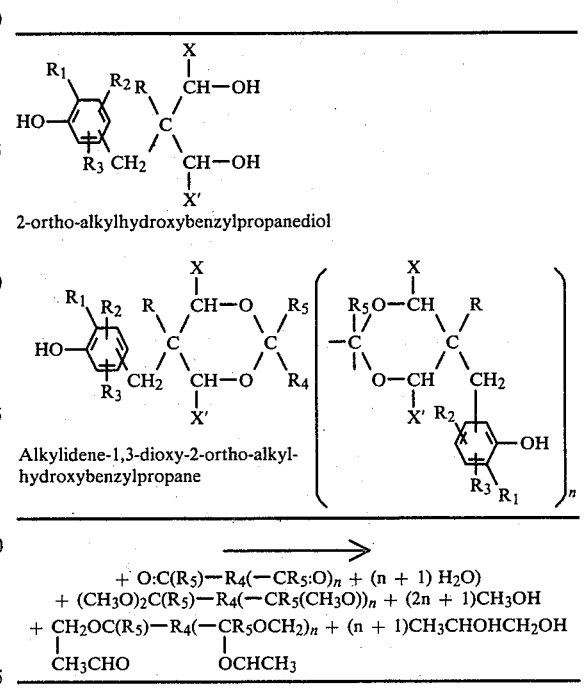

2-ortho-alkylhydroxybenzylpropanediol

Alkylidene-1,3-dioxy-2-ortho-alkyl-hydroxybenzylpropane

+ $O{:}C(R_5)$—$R_4$(—$CR_5{:}O)_n$ + (n + 1) H₂O
+ $(CH_3O)_2C(R_5)$—$R_4$(—$CR_5(CH_3O))_n$ + (2n + 1)CH₃OH
+ CH₂OC($R_5$)—$R_4$(—$CR_5OCH_2)_n$ + (n + 1)CH₃CHOHCH₂OH
  |                  |
  CH₃CHO         OCHCH₃

Preferred process conditions for the condensation reaction of the 2-alkyl-hydroxybenzylpropanediol and carbonyl compound derivative starting materials include heating the materials at 50° to 160° C., suitably in the presence of an acidic condensation catalyst such as sulfuric acid, ethanesulfonic acid, or zinc chloride. The volatile reaction by-product water or alcohol can be removed to displace the reaction equilibrium in the desired direction by application of vacuum or the use of an entraining solvent such as heptane or toluene.

When the Z group comprises a cycloalkylidene group

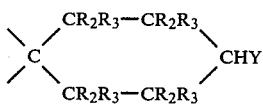

(in which $R_2$, $R_3$, and Y are as previously defined), the condensing agent is a cycloalkanone

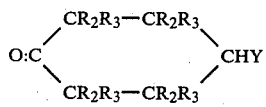

or an easily displaced ketal thereof, which can be a dialkyl ketal or a cyclic alkylene ketal. Reaction equations and conditions closely parallel the preparation of compounds of the invention in which Z is an alkylidene group.

When the Z group comprises a phosphorus ester group, the condensing agent is a phosphorylating agent which can be a phosphorus halide or a conveniently displaced phosphorus ester, for example a phenyl ester or a lower alkyl ester having not over 4 carbon atoms in each alkyl group.

The phosphorylating agent has linked to each phosphorus atom from one to three replaceable groups, such as halogen, phenyl, or lower alkyl linked to phosphorus through oxygen, and can also have groups that are not replaced in the reaction with the ortho-alkylhydroxybenzylpropanediol, such as oxygen-linked alkyl having more than 4 carbon atoms, oxygen-linked alkylphenol and polyhydric phenol groups, and organic groups linked to phosphorus through carbon. The replaceable groups on the phosphorylating agent can all be replaced simultaneously in a single reaction step, or successively in stages using the same or different reactants in each stage.

Phosphorylating agents having one phosphorus atom and three replaceable groups include phosphorus trichloride, phosphorus tribromide, phosphorus oxychloride, trimethyl phosphite, triethyl phosphite, tri-isopropyl phosphite, triphenyl phosphite, diphenyl phosphorochloridite, phenylphosphorodichloridite, and phenyl diethyl phosphite.

Phosphorylating agents having two replaceable groups per phosphorus atom include 2-ethylhexyl phosphorodichloridite, 2,4-di-t-butylphenyl phosphorodichloridate, isodecyl diphenyl phosphite, hexacosanyl diphenyl phosphite, dimethyl bisphenol A phosphite, tetraphenyl 4,4'-butylidenebis(2-t-butyl-5-methylphenol)diphosphite, n-butanephosphonous dichloride, diphenyl 2-ethylhexanephosphonite, diphenyl methanephosphonate, p-t-butyl benzenephosphonyl dichloride, diphenyl P-3,5-di-t-butyl-4-hydroxybenzylphosphonate, and tetraphenyl 1,6-hexanediphosphite. Phosphorylating agents having one replaceable group per phosphorus atom include methyl di(nonylphenyl) phosphite, di-n-hexyl phosphorochloridite, di-isooctyl phenyl phosphite, di-p-t-amylphenyl phosphorochloridate, and phenyl p-t-octylphenyl benzenephosphonate.

Reactions of a 2-ortho-alkylhydroxybenzylpropane-1,3-diol with a phosphorylating agent provide singly linked phosphorus ester propanediol compounds of this invention as well as doubly linked phosphorus ester propanediol compounds of this invention according to the proportions of reactants used. Singly linked phosphorus ester propanediol compounds are obtained by reaction of 2 moles of phosphorylating agent, with preferably a moderate excess over the calculated proportion, per mole of 2-ortho-alkylhydroxybenzyl-1,3-propanediol. Doubly linked phosphorus esters are obtained by reaction of one mole of phosphorylating agent per mole of 2-ortho-alkylhydroxybenzylpropanediol. One stage reactions of a 2-ortho-alkylpropanediol with phosphorylating agent to prepare propanediol compounds of the invention are shown in Schemes 3 and 4.

SCHEME 3

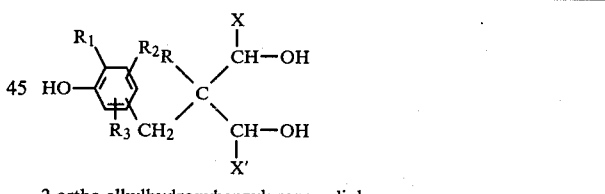

2-ortho-alkylhydroxybenzylpropanediol

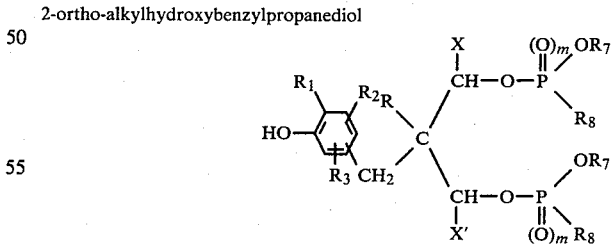

Singly linked phosphorus ester

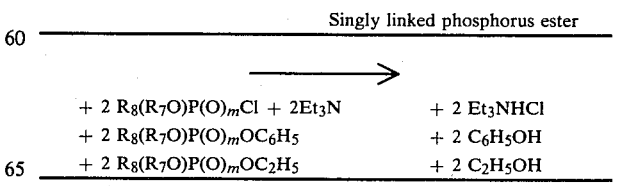

SCHEME 4

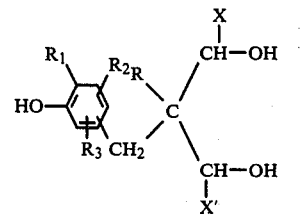

2-ortho-alkylhydroxybenzylpropanediol

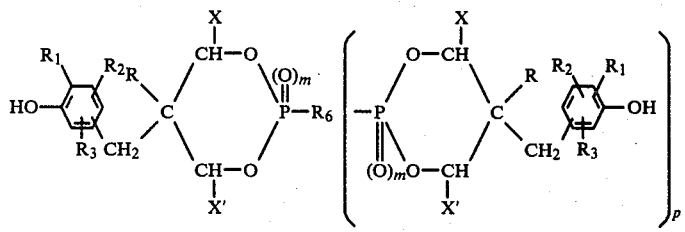

Doubly linked phosphorus ester

| | →  | |
|---|---|---|
| $R_6(P(O)_mCl_2)_{p+1}$ + 2p + 2 Et$_3$N | | 2p + 2 Et$_3$NHCl |
| $R_6(P(O)_m(OC_6H_5)_2)_{p+1}$ | | 2p + 2 C$_6$H$_5$OH |
| $R_6(P(O)_m(OC_2H_5)_2)_{p+1}$ | | 2p + 2 C$_2$H$_5$OH |

Multistage preparations wherein a 2-ortho-alkylhydroxybenzylpropanediol reacts with a phosphorylating agent to give a proanediol compound having replaceable groups which are replaced in subsequent reactions to give a propanediol compound of the invention are illustrated in Schemes 5A and 5B. The intermediate can itself be a propanediol compound of this invention.

Scheme 5A—PROPANEDIOL COMPOUND INTERMEDIATES

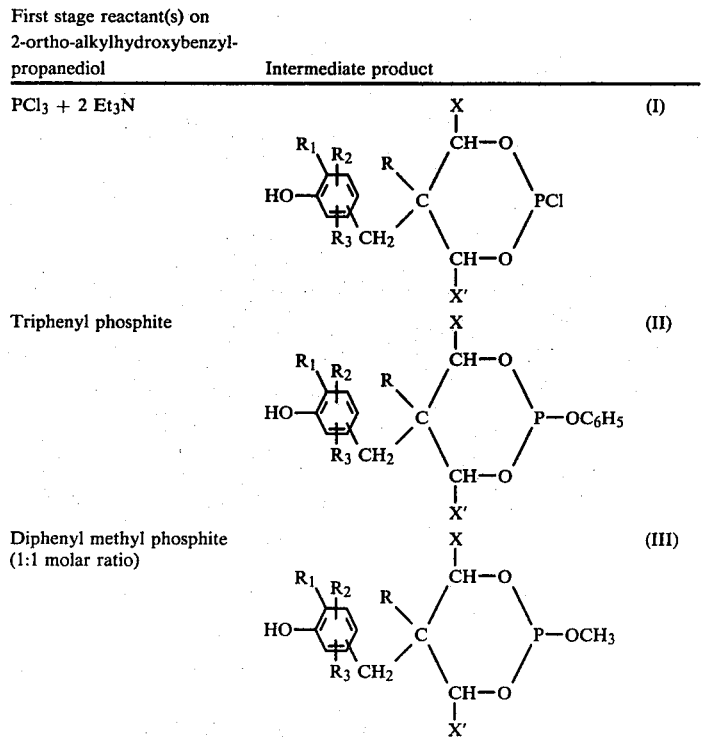

-continued

| First stage reactant(s) on 2-ortho-alkylhydroxybenzyl-propanediol | Intermediate product |
|---|---|
| Diphenyl methyl phosphite (2 moles phosphite/1 mole ortho-alkylhydroxybenzyl-propanediol) | 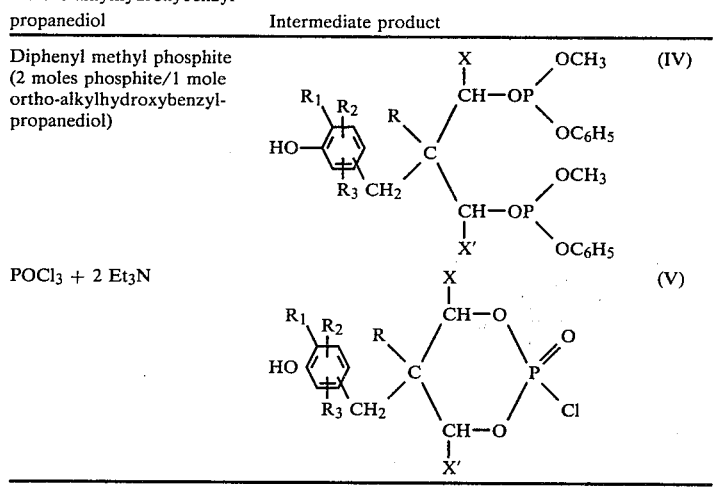 (IV) |
| $POCl_3 + 2\ Et_3N$ | (V) |

Scheme 5B—MULTISTAGE PROPANEDIOL COMPOUND PRODUCTS

| Second stage reactants | Propanediol Compound Product |
|---|---|
| $n\text{-}C_{12}H_{25}OH + (I) + Et_3N$ | |
| $HO(CH_2)_{10}OH + 2\ (I) + 2Et_3N$ | |
| Bisphenol A + (III) | |
| 1,1,3-tris(2-methyl-4-hydroxy-5-t-butylphenyl)butane + 3 (II) | |

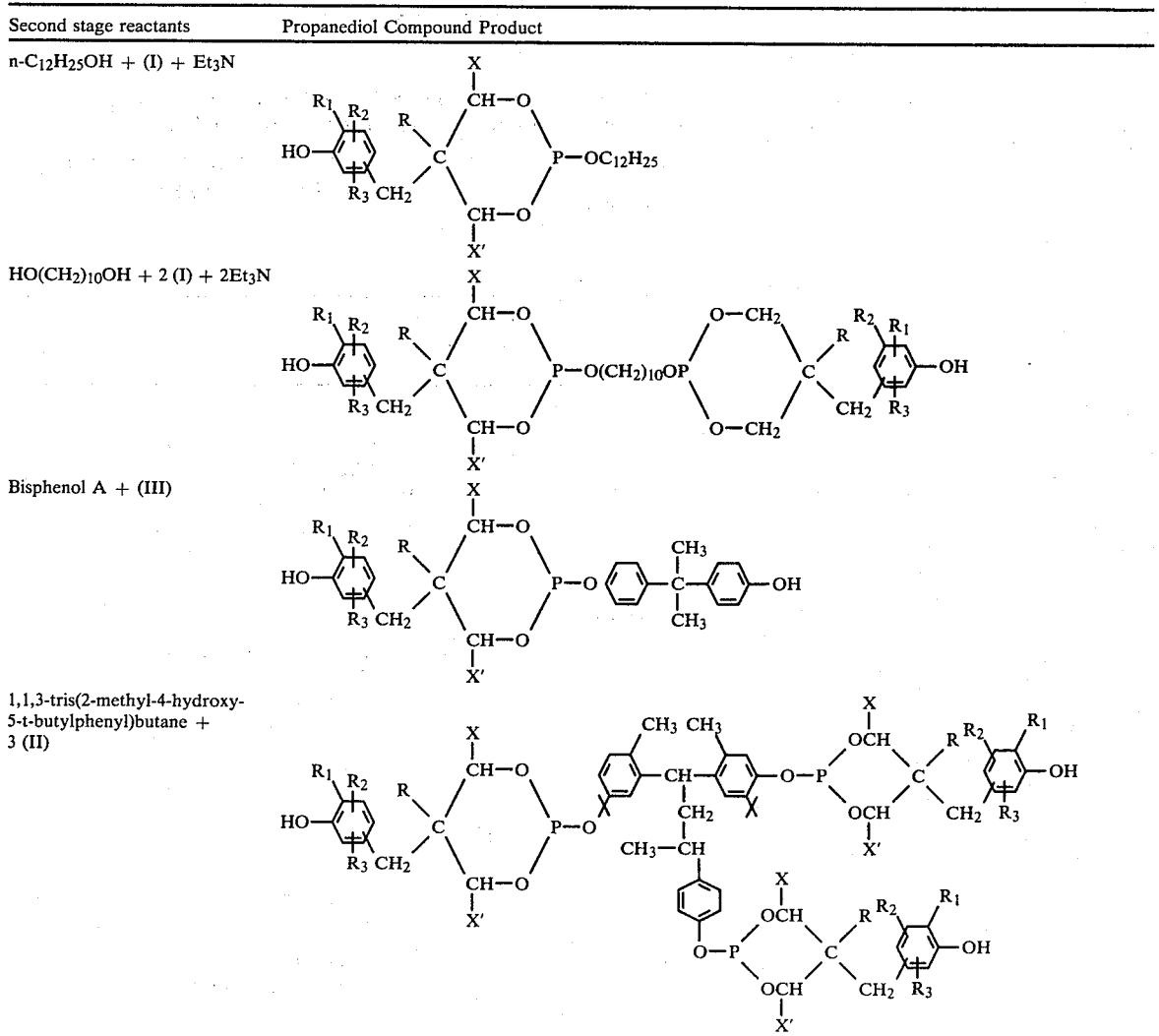

| Second stage reactants | Propanediol Compound Product |
|---|---|
| Tris(2-hydroxyethyl isocyanurate) + 3 (III) | *(structure shown)* |
| 3,5-di-t-butyl-4-hydroxybenzyl chloride + (IV) | *(structure shown)* |
| 4 C₁₈H₃₇OH + (IV) | *(structure shown)* |
| 2 3,5-di-t-butyl-4-hydroxy-benzyl chloride + (IV) | *(structure shown)* |
| 2-ethylhexanol + (V) + Et₃N | *(structure shown)* |
| 2,2-dimethylpropane-1,3-diol + (V) + 2 Et₃N | *(structure shown)* |

In the reactions of phosphorus halides shown in Schemes 3,4,5A, and 5B the use of triethylamine as an acid acceptor is indicated. Many other acid acceptors can be used with equal convenience; essentially any anhydrous organic or inorganic base can be used. Preferred acid acceptors include aliphatic, aromatic, and heterocyclic tertiary amines, for example trimethyl amine, diethylaniline, pyridine, and N-ethylmorpholine, also anhydrous ammonia, alkali metal bases such as sodium metal, sodium hydride, and potassium t-butoxide, or phenolates and alcoholates of barium, calcium, and lead can be used.

Preferred process conditions for the condensation reaction of substituted 2-ortho-alkylhydroxybenzyl-propanediol and phosphorylating agents are as follows:

Where phosphorus halide phosphorylating agents and acid acceptors are used, the reacting materials are brought together and allowed to react at −20° to about 80° C., suitably in an anhydrous solvent that assists the reaction and subsequent removal of the neutralized acid acceptor reaction product. Preferred solvents include hexane, diethyl ether, tetrahydrofuran, and di(2-methoxyethyl) ether. When lower alkyl phosphorus esters are used, the reactants are suitably heated in the 40° to 130° C. range while allowing the lower alkanol produced in the reaction to distil out, suitably assisted by applying subatmospheric pressure. Solvents or catalysts are not usually required with this method.

When phenyl phosphorus esters are used the reaction is suitably conducted in the 100° to 160° C. range, preferably in the presence of an alkaline catalyst such as calcium hydroxide, metallic sodium, sodium hydroxide, potassium carbonate, or barium oxide. Any alkaline catalyst is suitable whose 1% aqueous solution has a pH of 10 or higher. Phenol produced by the reaction of a phenyl phosphorus ester condensing agent is suitably removed by vacuum distillation to a pot temperature of approximately 190° C., leaving the desired product as the non-volatile residue.

The indicated reactions proceed in each instance to give the desired products in sufficiently high yield to enable them to be easily isolated from the reaction mixture by solvent removal, crystallization, or other known techniques. 2-Ortho-alkylhydroxybenzyl-1,3-propanediol compounds of this invention prepared by applying the methods outlined are shown in TABLE 1.

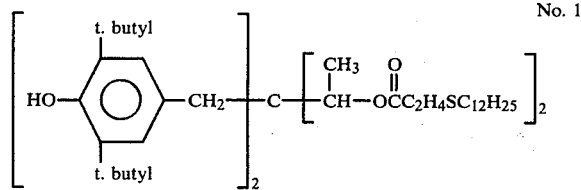

3,3-Bis(3',5'-di-t-butyl-4'-hydrobenzyl)2,4-pentanediol-di(3-n-dodecylthiopropionate)

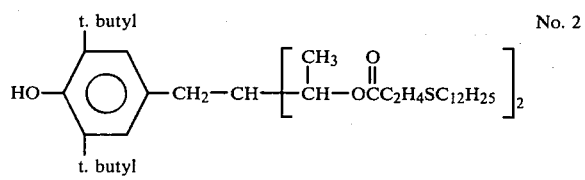

3(3',5'-di-t-butyl-4'-hydroxybenzyl)2,4-pentanedioldi(3-n-dodecylthiopropionate)

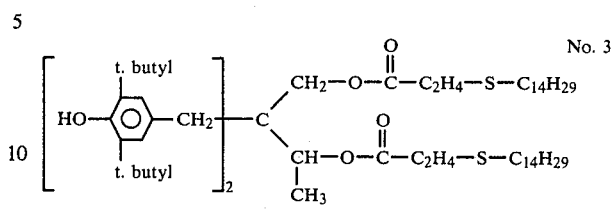

2,2-Bis(3',5'-di-t-butyl-4'-hydroxybenzyl)1,3-butanedioldi(3-n-tetradecylthiopropionate)

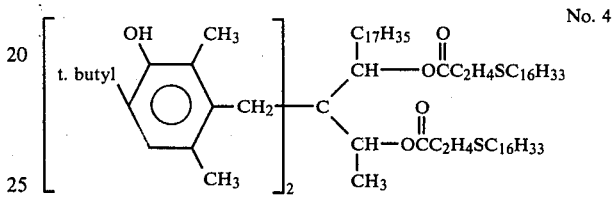

3,3-Bis(4'-t-butyl-2',6'-dimethyl-3'-hydroxybenzyl)2,4-heneicosanedioldi(3-n-hexadecylthiopropionate)

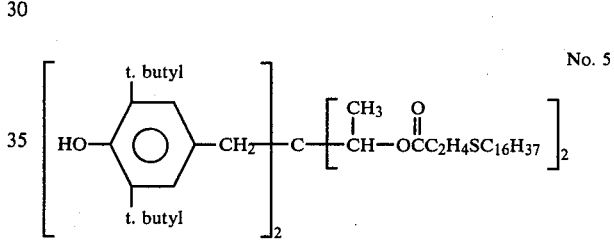

3,3-Bis(3',5'-di-t-butyl-4'-hydroxybenzyl)2,4-pentanedioldi(3-n-octadecylthiopropionate)

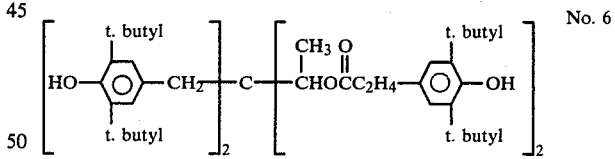

3,3-Bis(3',5'-di-t-butyl-4'-hydroxybenzyl)2,4-pentanedioldi(3,5-di-t-butyl-4-hydroxyhydrocinnamate)

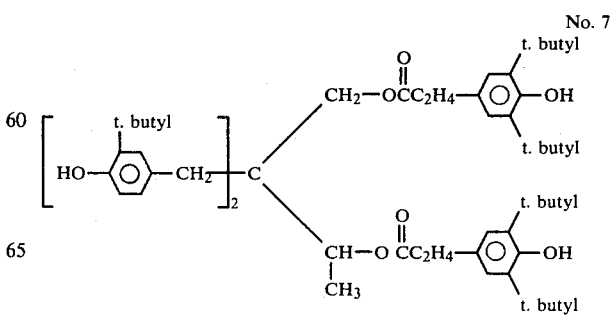

2,2-Bis(3′-t-butyl-4-hydroxybenzyl)1,3-butanediol-
di(3,5-di-t-butyl-4-hydroxyhydrocinnamate)

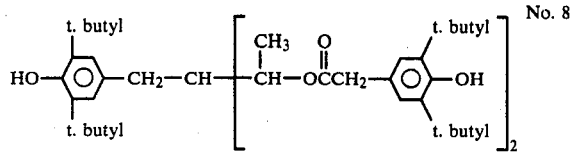

3(3′,5′-di-t-butyl-4′-hydroxybenzyl)2,4-pentanediol-
di(3,5-di-t-butyl-4-hydroxyhydrocinnamate)

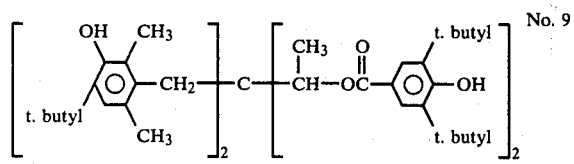

3,3-Bis(4′-t-butyl-2′,6′-dimethyl-3′-hydroxybenzyl)2,4-
pentanedioldi(3,5-di-t-butyl-4-hydroxybenzoate)

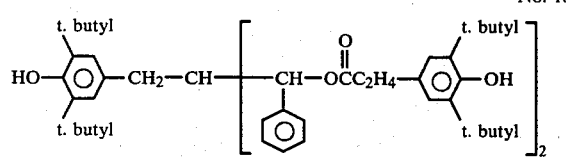

2(3′,5′-di-t-butyl-4′-hydroxybenzyl)1,3-diphenyl-
propanedioldi(3,5-di-t-butyl-4-hydroxyhydrocinna-
mate)

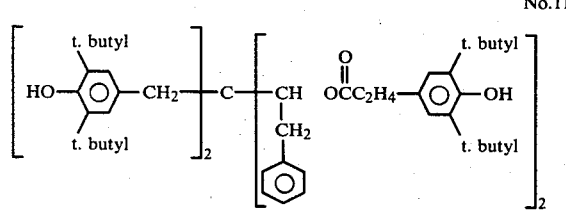

3,3-Bis(3′,5′-di-t-butyl-4′-hydroxybenzyl)1,5-diphenyl-
pentane-2,4-di(3,5-di-t-butyl-4-hydroxyhydrocinna-
mate)

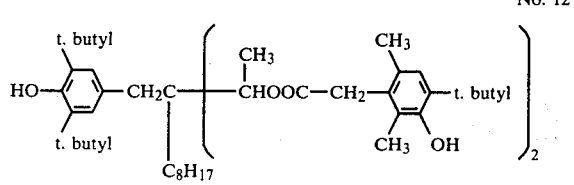

3-octyl-3(3′,5′-di-t-buyyl-4′-hydroxybenzyl)2,4-pen-
tanedioldi(2,6-dimethyl-3-hydroxy-4-t-butylhydrocin-
namate)

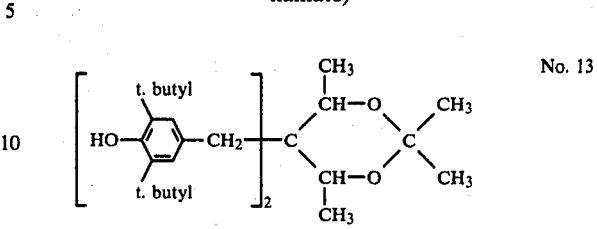

3,3-Bis(3′,5′-di-t-butyl-4′-hydroxybenzyl)2,4-(2,2-
propylidenedioxy)pentane

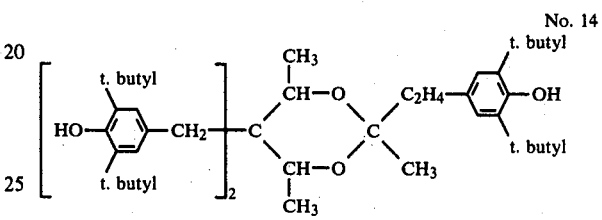

3,3-Bis(3′,5′-di-t-butyl-4′-hydroxybenzyl)-2,4-(4(3′,5′-di-
t-butyl-4′-hydroxyphenyl)2,2-butylidenedioxy)pentane

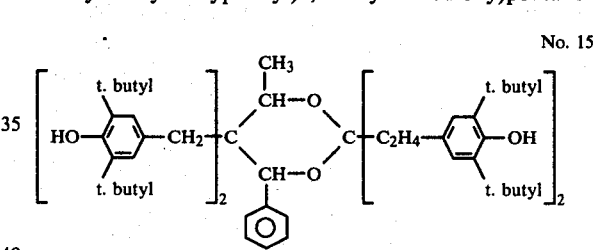

2,2-Bis(3′,5′-di-t-butyl-4′-hydroxybenzyl)-1,3-(1,5-di-t-
butyl-4′-hydroxyphenyl)-3,3-pentylidenedioxy)-1-
phenylbutane

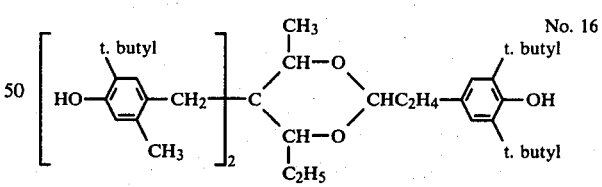

3,3-Bis(2′-methyl-4′-hydroxy-5′-t-butylbenzyl)-2,4-
(3(3′,5′-di-t-butyl-4′-hydroxyphenyl)1,1-propylidenedi-
oxy)hexane

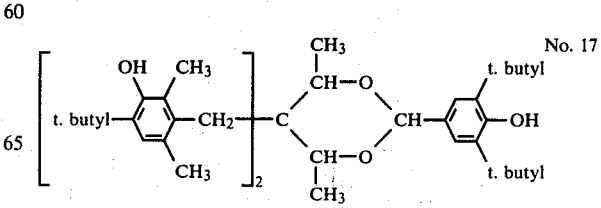

3,3-Bis(4'-t-butyl-2',6'-dimethyl-3'-hydroxybenzyl)-2,4-(3',5'-di-t-butyl-4'-hydroxybenzylidenedioxy)pentane No. 18

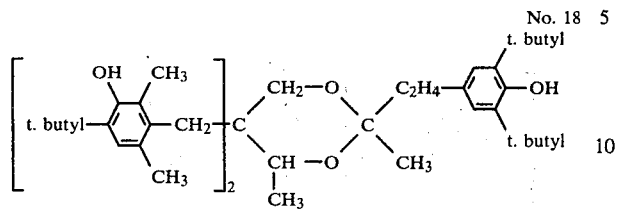

2,2-Bis(4'-t-butyl-2',6'-dimethyl-3'-hydroxybenzyl)-1,3-(4(3',5'-di-t-butyl-4'-hydroxyphenyl)2,2-butylidenedioxy)butane No. 19

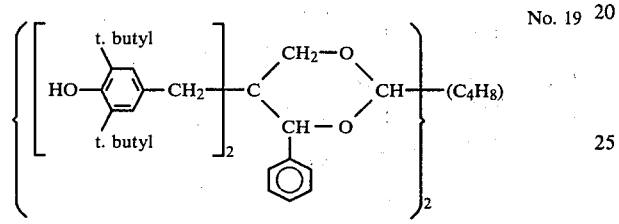

Hexane-1,1,6,6-di-ylidenebis(1,3-dioxy-2,2-(bis-3',5'-di-t-butyl-4'-hydroxybenzyl)-1-phenylpropane No. 20

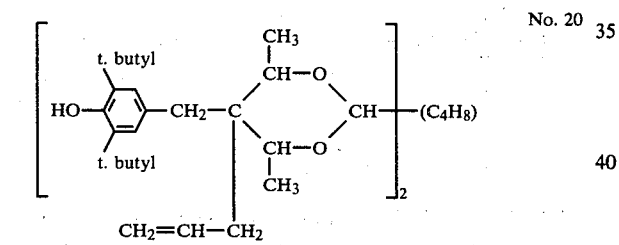

Hexane-1,1,6,6-di-ylidenebis(2,4-dioxy-3-allyl-3-(3',5'-di-t-butyl-4'-hydroxybenzyl)pentane No. 21

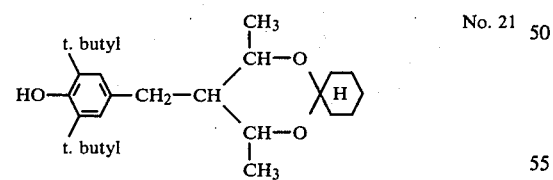

3-(3',5'-di-t-butyl-4'-hydroxybenzyl)cyclohexylidene-2,4-dioxy pentane

No. 22

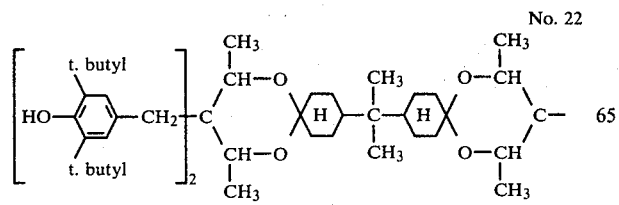

-continued

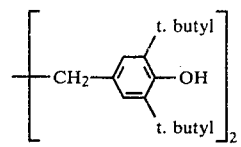

4,4'-isoproylidenedi(3,3-bis(3'-5'-di-t-butyl-4'-hydroxybenzyl)cyclohexylidene-2,4-dioxy pentane No. 23

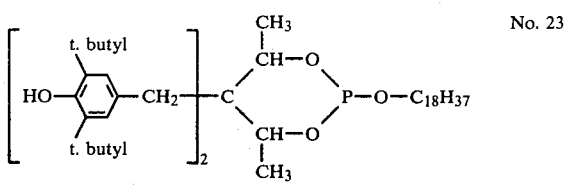

3,3-Bis(3',5'-di-t-butyl-4'-hydroxybenzyl)2,4-pentanediol cyclic n-octadecyl phosphite No. 24

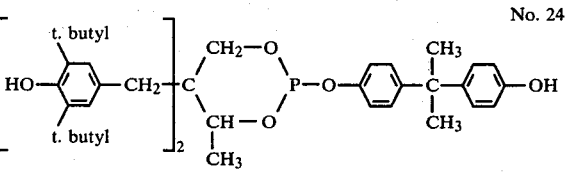

2,2-Bis(3',5'-di-t-butyl-4'-hydroxybenzyl)1,3-butanediol cyclic 4(p-hydroxyphenyl-2-propyl)phenyl phosphite No. 25

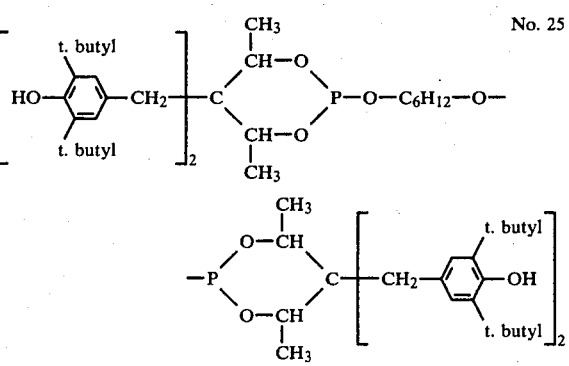

1,6-Hexamethylenebis(cyclic phosphite of 3,3-bis(3',5'-di-t-butyl-4'-hydroxybenzyl 2,4-pentadediol)

No. 26

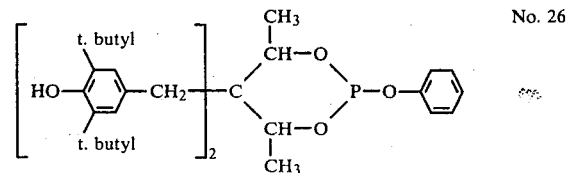

3,3-Bis(3',5'-di-t-butyl-4'-hydroxybenzyl)2,4-pentanediol cyclic phenyl phosphite.

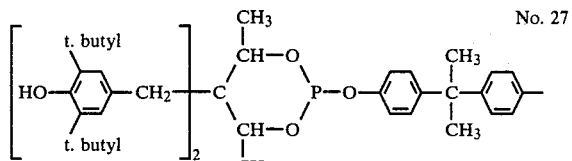

No. 27

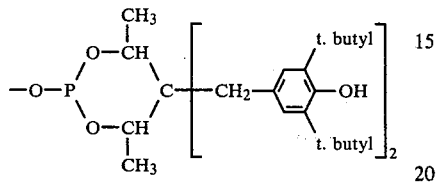

4,4'-isopropylidenedi(phenyl cyclic phosphite of 3,3-bis(3',5'-di-t-butyl-4'-hydroxybenzyl)2,4-pentanediol)

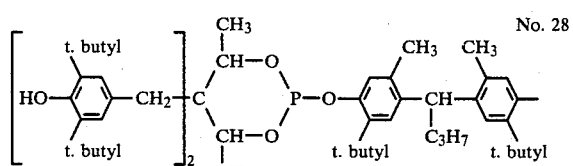

No. 28

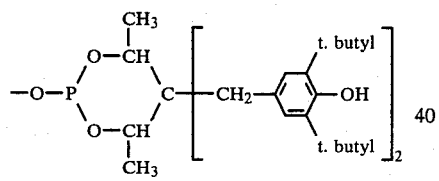

4,4'-b-butylidenedi(2-t-butyl-5-methylphenyl cyclic phosphite of 3,3-bis(3',5'-di-t-butyl-4'-hydroxybenzyl)2,4-pentanediol)

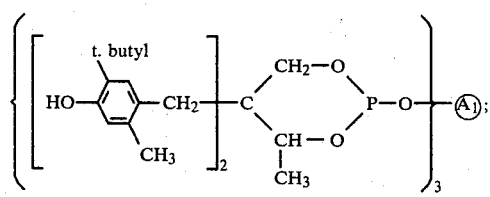

No. 29

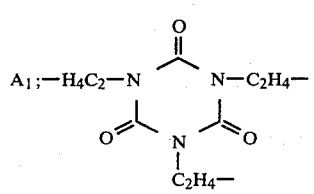

2,4,6-Trioxotriazine-1,3,5-tris(ethyl cyclic phosphite of 2,2-bis(2'-methyl-4'-hydroxy-5'-t-butylbenzyl)1,3-butanediol).

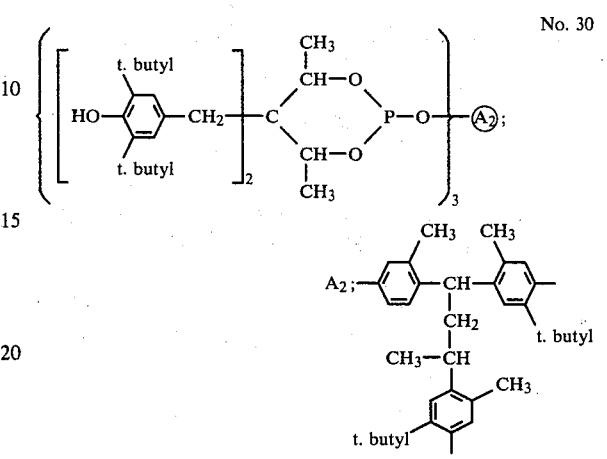

No. 30

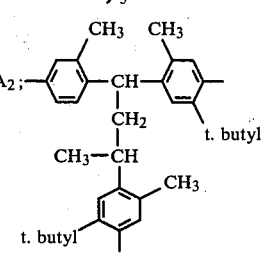

1,1,3-Butylidynetris(2'-methyl-5'-t-butylbenzene-4'-yl cyclic phosphite of 3,3-bis(3',5'-di-t-butyl-4'-hydroxybenzyl) 2,4-pentanediol.

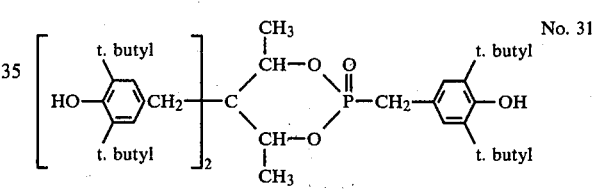

No. 31

3,3-Bis(3'5'-di-t-butyl-4'-hydroxybenzyl)2,4-pentanediol cyclic 3,5-di-t-butyl-4-hydroxybenzylphosphonate.

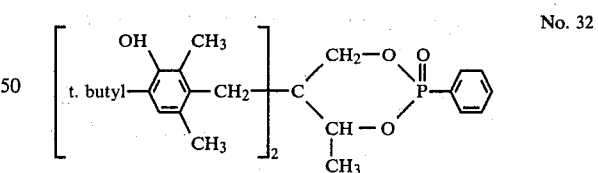

No. 32

2,2-Bis(4'-t-butyl-2',6'-dimethyl-3'-hydroxybenzyl)1,3-butanediol cyclic benzenephosphonate.

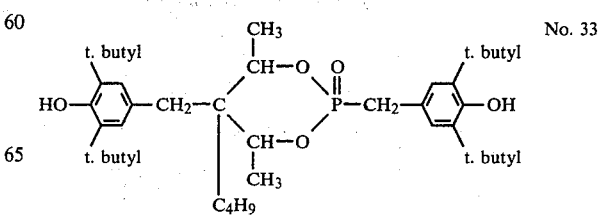

No. 33

3-Butyl-3(3′,5′-di-t-butyl-4′-hydroxybenzyl)2,4-pentanediol cyclic 3,5-di-t-butyl-4-hydroxybenzyl phosphonate.

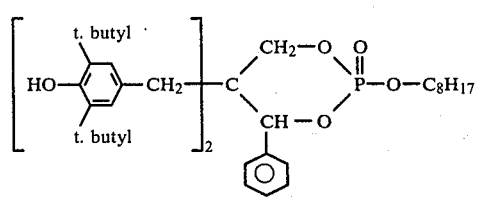

2,2-Bis(3′,5′-di-t-butyl-4′-hydroxybenzyl)-1-phenyl propanediol cyclic n-octyl phosphate.

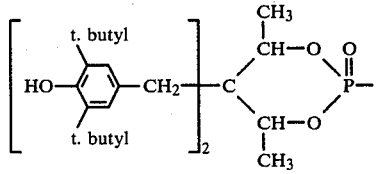

2,2-Dimethylpropane-1,3-bis(cyclic phosphate of 3,3-bis(3′,5′-di-t-butyl-4′-hydroxybenzyl)2,4-pentanediol)

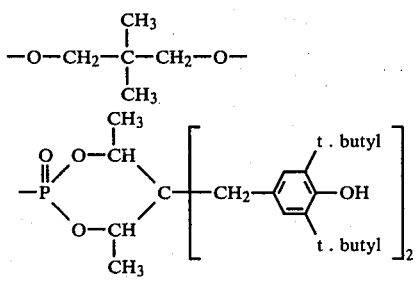

3,3-Bis(3′,5′-di-t-butyl-4′-hydroxybenzyl)2,4-pentanediol bis(di-n-dodecyl phosphite).

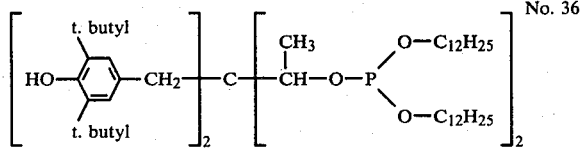

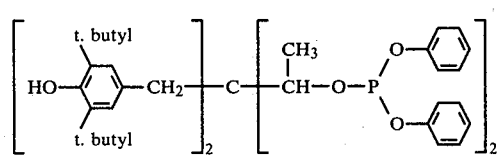

3,3-Bis(3′,5′-di-t-butyl-4′-hydroxybenzyl)2,4-pentanediol bis(diphenyl phosphite).

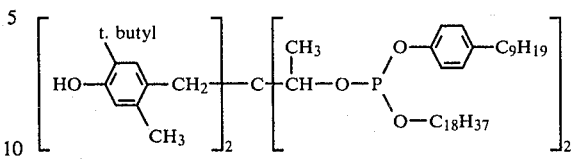

3,3-Bis(2′-methyl-5′-t-butyl-4′-hydroxybenzyl)2,4-pentanediol bis(n-octadecyl p-nonylphenyl phosphite).

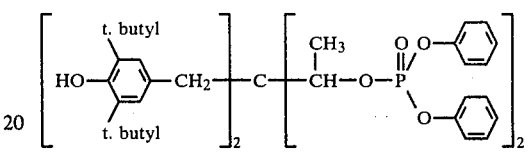

3,3-Bis(3′,5′-di-t-butyl-4′-hydroxybenzyl)2,4-pentane diolbis (diphenyl phosphate).

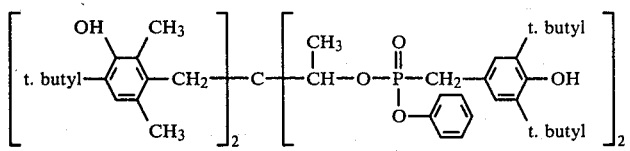

3,3-Bis(4′-t-butyl-2′,6′-dimethyl-3′-hydroxybenzyl)2,4-pentanediol-bis(O-phenyl P-(3,5-di-t-butyl-4-hydroxybenzyl)phosphonate).

Synthetic resins that can be stabilized with compositions comprising an ortho-alkylhydroxybenzylpropanediol compound according to this invention include alphaolefin polymers such as polyethylene, polypropylene, polybutene, poly-3-methylbutene, or copolymers thereof such as ethylene-vinylacetate copolymer, ethylenepropylene copolymer, polystyrene, polyvinylacetate, acrylic ester resins, copolymers from styrene and another monomer (for example, maleic anhydride, butadiene, acrylonitrile and so on), acrylonitrile-butadiene-styrene copolymer, acrylic acid ester-butadiene-styrene copolymer, methacrylic acid ester-butadiene-styrene copolymer, methacrylate ester resin such as polymethylmethacrylate, polyvinylalcohol, ethylene and butylene terephthalate polyesters, diaminoalkane/alkylene-dicarboxylic and lactam polymer polyamides, polycarbonate, polyacetal, polyurethane, cellulosic resin, or phenolic resin, urea resin, melamine resin, epoxy resin, unsaturated polyester, silicone resin, halogen-containing resins such as polyvinyl chloride, polyvinylidene chloride, polyvinylidene fluoride and copolymers thereof, and further rubbers such as isoprene rubber, chloroprene rubber, and blends of the above resins.

Stabilizer compositions comprising an ortho-alkylhydroxybenzylpropanediol compound according to this invention can be formulated and marketed in liquid, solid, and paste forms. An inert solvent can be used to facilitate handling. The propanediol compound and known polymer stabilizers can be solubilized in one another by heating, such as at 70°–160° C. for up to 4 hours, and then allowing the resulting melt to cool and harden sufficiently to be flaked and ground.

Known polymer stabilizers can be used in synthetic resin compositions together with the propanediol compound stabilizers of this invention and can be admixed with the latter. Such stabilizers include thiodipropionic acid esters, polyvalent metal salts of carboxylic acids, organic phosphites, 1,2-epoxides, polyhydric alcohols, polyhydric alcohol 3-alkylthiopropionic acid esters, ultraviolet absorbers and heavy metal deactivators. Representative thiodipropionic acid esters include di-n-dodecyl thiodipropionate, dihexadecyl thiodipropionate, distearyl thiodipropionate, no-octyl eicosanyl thiodipropionate and n-octadecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference. When thiodipropionate esters are used the concentration based on 100 parts of polymer can range from 0.05 to about 0.75 parts by weight.

Representative polyvalent metal salts include zinc, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 column 20 line 35 is here incorporated by reference. When metal salts are used the concentration based on 100 parts by weight of polymer can range from 0.1 to about 3 parts by weight.

Representative organic phosphites include triisodecylphosphite, tris(nonylphenyl phosphite), and 4,4'-isopropylidene diphenol alkyl($C_{12}$-$C_{15}$)phosphite. A comprehensive disclosure of useful organic phosphites by M. Minagawa in U.S. Pat. No. 3,849,370 column 13 line 63 to column 16 line 48 is here incorporated by reference. Typical use concentrations of organic phosphites are in the range from 0.02 part to about 2 parts by weight per 100 parts of polymer being stabilized.

Representative 1,2-epoxides that can be used in stabilizer compositions according to this invention include epoxysoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference. Typical use concentrations of 1,2-epoxides range from 0.3 to about 6 parts by weight per 100 parts of synthetic resin composition.

Aliphatic polyhydroxy compounds can be included with stabilizer compositions of this invention in amounts corresponding to 0.1 to about 1 part per 100 parts of polymer being stabilized. Typical aliphatic polyhydroxy compounds are glycerol, polyglycerol, mono- di-, and tri-pentaerythritol, mannitol, sorbitol, and partial esters of these with saturated and unsaturated fatty acids having 6 to 22 carbon atoms.

3-Alkylthio propionates of polyhydric alcohols can be included in stabilizer compositions of this invention in amounts corresponding to 0.02 to about 1 part per 100 parts of synthetic resin being stabilized. The propionate esters have 4 to about 34 carbon atoms in the alkylthiopropionate group, 2 to about 15 carbon atoms in the polyhydric alcohol group and 2 to about 8 ester groups in the molecule. Representative propionate esters are 2,2-dimethylpropanediol bis(3-n-dodecylthio-2-methylpropionate), pentaerythritol tetrakis(3-n-octylthiopropionate) and tris(3-n-octadecylthiopropionyloxyethyl)isocyanurate. For a further listing of useful 3-alkylthiopropionates the disclosure of A. Onishi U.S. Pat. No. 3,629,194 can be consulted.

Ultraviolet absorbers can be included in stabilizer compositions of this invention in amounts corresponding to 0.05 to about 1 part per 100 parts of synthetic resin being protected. Typical ultraviolet absorbers are 2-hydroxybenzophenones such as 2-hydroxy-4-n-octyloxybenzophenone and 2,4-dihydroxybenzophenone, and 2-(2'hydroxyphenyl)benzotriazoles such as 2-(2'-hydroxy-5'-methylphenylbenzotriazole and 2-(2'-hydroxy-5'-t-butylphenyl)5,6-dichlorobenzotriazole.

For a further listing of many useful ultraviolet absorbers the disclosure of U.S. Pat. No. 3,395,112 of July 30, 1968, particularly column 14 line 40 to column 19 line 33, can be consulted. Stabilizer compositions according to this invention that protect synthetic resin compositions used in contact with materials containing heavy metals and their compounds, as in insulating materials for copper based electrical conductors or in compositions pigmented with heavy metal containing pigments such as rouge, talc, and iron-bearing asbestos, can contain heavy metal deactivators that counteract the prodegradant effect of the heavy metal on synthetic resin compositions that would be satisfactorily stabilized in the absence of heavy metal. Heavy metal deactivators that can be used in stabilizer compositions according to this invention include melamine, dicyandiamide, oxanilide, N,N'-disalicyloylhydrazine, 3-salicyloylamido-1,2,4-triazole, as well as the heavy metal deactivators disclosed by M. Minagawa in U.S. Pat. Nos. 3,549,572 (column 5 line 19 to column 10 line 23), 3,629,181 (column 5 line 15 to column 9 line 54), 3,673,152 (column 4 line 47 to column 8 line 62), and 3,849,370 (column 5 line 5 to column 13 line 45). These disclosures are here incorporated by reference.

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylene-vinyl acetate copolymers and others.

The Examples that follow illustrate the invention without limiting its scope. Synthetic Examples 1 through 10 describe the preparation of different ortho-alkylhydroxybenzylpropanediol compounds of this invention. Examples 1 through 10 illustrate the use of propanediol compound stabilizers of this invention and stabilizer compositions comprising propanediol compounds of this invention in the stabilization of olefin polymers, a vinyl chloride polymer, an ABS polymer, a polycarbonate, and a polyamide.

SYNTHETIC EXAMPLE—1

Preparation of 3,3-Bis(3',5'-di-t-butyl-4'-hydroxybenzyl)2,4-pentanedioldi(3-n-octadecyl thiopropionate)— TABLE 1, compound 5.

3,3-Bis(3,5-di-t-butyl-4-hydroxybenzyl)pentanediol 54.0 g (0.1 mole) was dissolved in pyridine-toluene solvent, and toluene solution of 3-stearyl thiopropionylchloride 75.1 g (0.2 mole) was added therein dropwise. After addition, the whole was heated to 70° C. and reacted for 7 hours. Precipitated pyridine hydrochloride was filtered and the solution was washed and dried. The solvent was stripped off and the residue was treated with methanol to give the compound named as a pale yellow powder of m.p. 48°-50° C.

By applying the method of this Example to the appropriate starting materials, the following ortho-alkylhydroxybenzylpropanediol compounds of Table 1 are prepared.

Synthetic Example 2 Compound No. 1 is made from 3,3-bis(3',5'-di-t-butyl-4'-hydroxybenzyl)-2,4-pentanediol and 3-n-dodecylthiopropionyl chloride.

Synthetic Example 3 Compound No. 3 is made from 2,2-bis(3',5'-di-t-butyl-4'-hydroxybenzyl)-1,3-butanediol and 3-n-octadecylthiopropionic acid chloride.

Synthetic Example 4 Compound No. 6 is made from 3,3-bis(3',5'-di-t-butyl-4'-hydroxybenzyl)-2,4-pentanediol and 3,5-di-t-butyl-4-hydroxyhydrocinnamic acid chloride.

Synthetic Example 5 Compound No. 2 is made from 3(3',5'-di-t-butyl-4'-hydroxybenzyl)-2,4-pentanediol and 3-n-dodecylthiopropionic acid chloride.

Synthetic Example 6 Compound No. 4 is made from 3,3-bis(4'-t-butyl-2',6'-dimethyl-3')hydroxybenzyl)-2,4-heneicosanediol and 3-n-hexadecylthiopropionic acid chloride.

Synthetic Example 7 Compound No. 9 is made from 3,3-bis(4'-t-butyl-2',6'-dimethyl-3'-hydroxybenzyl)2,4-pentanediol and 3,5-di-t-butyl-4-hydroxybenzoyl chloride.

Synthetic Example 8 Compound No. 7 is made from 3,3-bis(3'-t-butyl-4'-hydroxy-benzyl)2,4-pentanediol and 3,5-di-t-butyl-4-hydroxy-hydrocinnamic acid chloride.

Synthetic Example 9 Compound No. 12 is made from 3-n-octyl-3-(3',5'-di-t-butyl-4'-hydroxy-benzyl)-2,4-pentanediol and 4-t-butyl-2,6-dimethyl-3-hydroxyphenylacetic acid chloride.

Synthetic Example 10 Compound No. 32 is made from 2,2-Bis(4'-t-butyl-2',6'-dimethyl-3'-hydroxybenzyl)-1,3-butanediol and benzenephosphonyldichloride.

Synthetic Example 11 Preparation of 3,3-Bis(3',5'-di-t-butyl-4'-hydroxybenzyl)2,4-pentanediol bis(diphenyl phosphite)—Table 1 Compound No. 37.

3,3-Bis(3',5'-di-t-butyl-4'-hydroxybenzyl)-2,4-pentanediol 51.3 g (0.1 mole, triphenylphosphite 93 g (0.3 mole) and potassium carbonate 1.4 g were heated at 140°-150° C. for 3 hours under nitrogen, then distilled to remove 0.2 moles of phenol under reduced pressure to obtain the desired product as a viscous liquid.

By applying the method of this Example to the appropriate starting materials (in a 1:1 molar ratio except as specifically indicated), the following ortho-alkylhydroxybenzylpropanediol phosphorus ester compounds of Table 1 are prepared.

Synthetic Example 12 Compound No. 26 from 3,3-bis(3',5'-di-t-butyl-4'-hydroxybenzyl)-2,4-pentanediol and triphenyl phosphite.

Synthetic Example 13 Compound No. 23 from compound No. 26 and n-octadecanol.

Synthetic Example 14 Compound 25 from compound No. 26 per mole 1,6-hexanediol.

Synthetic Example 15 Compound No. 27 from 2 moles compound No. 26 per mole Bisphenol A.

Synthetic Example 16 Compound No. 28 from 2 moles compound No. 26 per mole 4,4'-n-butylidenebis(2-t-butyl-5-methylphenol).

Synthetic Example 17 Compound No. 29 from 3 moles 2,2-bis(2'methyl-4'-hydroxy-5'-t-butylbenzyl)-1,3-butanediol cyclic phosphite (itself prepared from the diol and triphenyl phosphite as for compound No. 26) per mole tris(2-hydroxyethyl)isocyanurate.

Synthetic Example 18 Compound No. 30 from 3 moles compound No. 26 per mole 1,1,3-tris(2'methyl-4'-hydroxy-5'-t-butylphenyl)butane.

EXAMPLES 1-1 TO 1-13

Substantially unstabilized polypropylene resin (Profax 6501 containing a trace of BHT for storage protection only) 100 parts by weight and sample compound (TABLE 2) 0.3 part by weight were mixed for 10 minutes by mixing and grinding at room temperature and milled at 180° C. for 6 minutes, followed by compression molding at 180° C. and 200 kg/cm$^2$ for 5 minutes, to obtain a smooth sheet of 1.0 mm in thickness.

Test specimens were cut off from the sheet and used to measure heat stability in a Geer oven at 160° C.

The sample compounds used and heat stability results obtained are shown in TABLE 2.

TABLE 2

| No. | SAMPLE COMPOUNDS | TIME TO BEGINNING OF DEGRADATION (hrs) |
|---|---|---|
| CONTROL | | |
| 1-1 | 3,3-bis(3,5-di-t-butyl-4-hydroxybenzyl)-2,4-pentanediol | 90 |
| 1-2 | 3,3-bis(3,5-di-t-butyl-4-hydroxybenzyl)-2,4-pentanedioldiacetate | 75 |
| 1-3 | Stearyl-3-(3,5-di-t-butyl-4-hydroxyphenyl)propionate | 140 |
| EXAMPLE | | |
| 1-1 | No. 1 (Table 1) | 520 |
| 1-2 | No. 3 (Table-1) | 510 |
| 1-3 | No. 5 (Table-1) | 535 |
| 1-4 | No. 6 (Table-1) | 495 |
| 1-5 | No. 9 (Table-1) | 420 |
| 1-6 | No. 14 (Table-1) | 485 |
| 1-7 | No. 19 (Table-1) | 435 |
| 1-8 | No. 22 (Table-1) | 450 |
| 1-9 | No. 25 (Table-1) | 425 |
| 1-10 | No. 29 (Table-1) | 460 |
| 1-11 | No. 32 (Table-1) | 390 |
| 1-12 | No. 35 (Table-1) | 375 |
| 1-13 | No. 40 (Table-1) | 485 |

The results of the heat stability test show that the ortho-alkylhydroxybenzylpropanediol compounds of this invention in the absence of other additives protect polypropylene over 2½ times as long as the conventional phenolic antioxidant or alkylhydroxybenzylpropanediol derivatives not of this invention.

EXAMPLES 2-1 TO 2-13

Substantially unstabilized polypropylene resin (Profax 6501, containing a trace of BHT antioxidant to protect the polymer during shipment and storage only) 100 parts by weight, dilaurylthiodipropionate 0.2 parts by weight, ortho-alkylhydroxybenzylpropanediol compound 0.1 part by weight were mixed for ten minutes by mixing and grinding at room temperature and milled and molded to make a sheet of 1.0 mm in thickness at 180° and 200 kg/cm$^2$ for 5 minutes. From this sheet were cut ten sample pieces of 10×20 mm of each formulation, and exposed on aluminum foil in a Geer air-circulating oven at 160° C. for heat stability examination. The time to the beginning of degradation was taken as the time when more than five sample pieces in ten of each formulation were discolored and brittle.

The sample compounds used and the results obtained are shown in TABLE 3.

TABLE 3

| No. | SAMPLE COMPOUNDS | TIME TO BEGINNING OF DEGRADATION (hrs) |
|---|---|---|
| CONTROL | | |
| 2-1 | 2,2-bis(3,5-di-t-butyl-4-hydroxybenzyl)-1,3-butanediol | 330 |
| 2-2 | Tris(3,5-di-t-butyl-4-hydroxyphenyl)phosphite | 390 |
| 2-3 | 1,1,3-tris(3-t-butyl-4-hydroxy-6-methylphenyl)butane | 420 |
| EXAMPLE | | |
| 2-1 | No. 3 (Table-1) | 1180 |
| 2-2 | No. 4 (Table-1) | 1210 |
| 2-3 | No. 7 (Table-1) | 1030 |
| 2-4 | No. 10 (Table-1) | 1020 |
| 2-5 | No. 15 (Table-1) | 1060 |
| 2-6 | No. 18 (Table-1) | 1030 |
| 2-7 | No. 21 (Table-1) | 970 |
| 2-8 | No. 24 (Table-1) | 1010 |
| 2-9 | No. 28 (Table-1) | 1200 |
| 2-10 | No. 31 (Table-1) | 970 |
| 2-11 | No. 34 (Table-1) | 930 |
| 2-12 | No. 36 (Table-1) | 910 |
| 2-13 | No. 38 (Table-1) | 1080 |

Each of the polypropylene samples of Examples 2-1 through 2-13 stabilized according to this invention with an ortho-alkylhydroxybenzylpropanediol compound had more than twice the heat stability of a control composition containing an outstandingly effective conventional phenolic stabilizer along with the same dilauryl thiodipropionate synergist, used in EXAMPLES 2-1 TO 2-13.

EXAMPLES 3-1 TO 3-12

Stabilized polyethylene resin (Hi-Zex 5100E, Mitsui Petrochemical Industries, Ltd. Japan) 100 parts by weight and a propanediol compound 0.15 part by weight were milled on a two roll mill for 5 minutes at 150° C. and then molded into a sheet of 1.2 mm thickness by compression molding at 150° C. and 180 kg/cm² for 5 minutes. The sheet was cut into sample pieces of 10×20 mm and tested for heat stability in the Geer oven at 148.5° C. in air on aluminum foil. The time to the beginning of degradation was taken as the time when more than five sample pieces in ten of each formulation were discolored and waxy. The stabilizer ingredients used and the results obtained are shown in Table 4.

TABLE 4

| No. | SAMPLE COMPOUNDS | TIME TO BEGINNING OF DEGRADATION (hrs) |
|---|---|---|
| CONTROL | | |
| 3-1 | NONE | 170 |
| 3-2 | 3-(3,5-di-t-butyl-4-hydroxybenzyl)-2,4-pentanediol | 235 |
| 3-3 | Thiodiethyleneglycol bis[3,5-di-t-butyl-4-hydroxyphenyl) propionate] | 280 |
| EXAMPLE | | |
| 3-1 | No. 2 (Table-1) | 360 |
| 3-2 | No. 5 (Table-1) | 425 |
| 3-3 | No. 8 (Table-1) | 370 |
| 3-4 | No. 11 (Table-1) | 410 |
| 3-5 | No. 12 (Table-1) | 345 |
| 3-6 | No. 16 (Table-1) | 380 |
| 3-7 | No. 21 (Table-1) | 335 |
| 3-8 | No. 23 (Table-1) | 365 |
| 3-9 | No. 27 (Table-1) | 385 |
| 3-10 | No. 33 (Table-1) | 400 |
| 3-11 | No. 37 (Table-1) | 355 |
| 3-12 | No. 39 (Table-1) | 335 |

Each of the polyethylene samples of Examples 3-1 through 3-12 stabilized with an ortho-alkylhydroxybenzylpropanediol compound of this invention had at least 100% greater heat stability than a control sample without added stabilizer.

EXAMPLES 4-1 to 4-11

ABS resin (Blendex III) 100 parts by weight, Zinc stearate 0.5 part by weight, titanium dioxide 5.0 parts by weight, and an ortho-alkylhydroxybenzylpropanediol sample compound 0.5 part by weight were mixed by grinding at room temperature for 10 minutes.

The compound was prepared by extruding the ground mixture using a 30 mm extruder at 30 rpm and 240° C. A sheet of 0.5 mm thickness was prepared by compression molding each extruded compound at 200 kg/cm² and 180° C. for 5 minutes. Each molded sheet was cut to the size of 40×150 mm, and subjected to heating at 135° C. for 20 hours.

The color of each sheet after heating for 20 hours was measured by the Hunter colorimeter and expressed in terms of whiteness, the better samples being indicated by higher numbers.

The propanediol stabilizer used in each example and the results observed as shown in TABLE 5.

TABLE 5

| No. | SAMPLE COMPOUNDS | WHITENESS |
|---|---|---|
| CONTROL | | |
| 4-1 | 3,3-bis(3,5-di-t-butyl-4-hydroxybenzyl)-2,4-pentanediol | 0.15 |
| 4-2 | 4,4'-butylidenebis(2-t-butyl-5-methylphenol) | 0.16 |
| 4-3 | Pentaerythritol tetrakis [3,5-di-t-butyl-4-hydroxyphenyl) propionate] | 0.25 |
| EXAMPLE | | |
| 4-1 | No. 1 (Table-1) | 0.37 |
| 4-2 | No. 4 (Table-1) | 0.36 |
| 4-3 | No. 6 (Table-1) | 0.34 |
| 4-4 | No. 7 (Table-1) | 0.30 |
| 4-5 | No. 13 (Table-1) | 0.30 |
| 4-6 | No. 17 (Table-1) | 0.34 |
| 4-7 | No. 22 (Table-1) | 0.31 |
| 4-8 | No. 26 (Table-1) | 0.32 |
| 4-9 | No. 30 (Table-1) | 0.33 |
| 4-10 | No. 31 (Table-1) | 0.35 |
| 4-11 | No. 35 (Table-1) | 0.31 |

Each of the ABS polymer samples of EXAMPLES 4-1 through 4-14 stabilized according to this invention with an ortho-alkylhydroxybenzylpropanediol compound had far superior whiteness than the control samples stabilized with the same zinc stearate as in EXAMPLES 4-1 through 4-11 along with a conventional polyhydric phenol stabilizer.

EXAMPLES 5-1 to 5-11

A clear sheet was prepared by kneading polyvinylchloride resin (Geon 103EP) 100 parts, dioctylphthalate 42 parts, epoxidized soybean oil 3 parts, zinc stearate 0.3 parts, barium stearate 0.5 parts, stearic acid 0.3 parts, and a propanediol sample compound 0.1 parts on a two roll mill at 175° C. for 5 minutes and then compression molding at 175° C. Then, a heat stability test was carried out in a Geer oven at 190° C. in an air atmosphere. The time to degradation was determined by the discoloration observed. The ortho-alkylhydroxybenzylpropanediol compound used and the results obtained are shown in TABLE 6.

TABLE 6

| No. | SAMPLE COMPOUNDS | TIME TO BEGINNING OF DEGRADATION YELLOWED Min. | BLACKENED Min. |
|---|---|---|---|
| CONTROL | | | |
| 5-1 | NONE | 30 | 40 |
| 5-2 | BHT | 35 | 45 |
| 5-3 | 3,3-bis(3,5-di-t-butyl-4-hydroxyphenyl)-2,4-pentanediol diacetate | 40 | 50 |
| EXAMPLE | | | |
| 5-1 | No. 2 (TABLE-1) | 60 | 75 |
| 5-2 | No. 5 (TABLE-1) | 70 | 85 |
| 5-3 | No. 8 (TABLE-1) | 60 | 70 |
| 5-4 | No. 11 (TABLE-1) | 70 | 80 |
| 5-5 | No. 15 (TABLE-1) | 70 | 80 |
| 5-6 | No. 20 (TABLE-1) | 60 | 70 |
| 5-7 | No. 23 (TABLE-1) | 70 | 85 |
| 5-8 | No. 29 (TABLE-1) | 55 | 65 |
| 5-9 | No. 34 (TABLE-1) | 55 | 70 |
| 5-10 | No. 37 (TABLE-1) | 65 | 70 |
| 5-11 | No. 40 (TABLE-1) | 60 | 70 |

Each of the polyvinyl chloride samples of EXAMPLES 5-1 through 5-11 stabilized according to this invention with an ortho-alkylhydroxybenzylpropanediol compound, along with epoxidized soybean oil, zinc stearate, and barium stearate, had at least 50% greater heat stability than a control sample containing a conventional hindered phenol along with the same epoxidized soybean oil, zind stearate, and barium stearate.

EXAMPLES 6-1 to 6-8

The propanediol compounds according to this invention have an excellent stabilizing effect on crosslinked polyethylene. Unstabilized low density polyethylene (Meltindex 2.0) 100 parts by weight, dilaurylthiodipropionate 0.2 part by weight, and propanediol sample compound as shown 0.2 part by weight were mixed by milling on a two roll mill at 110° C. for 10 minutes and then dicumyl peroxide (percumyl D, Nippon Oil and Fats Co., Ltd.) 2.0 parts by weight as added and further kneaded at the same temperature for two minutes. This sheet prepared on the mill was compression molded at 110° C. and 100 kg/cm² for 5 minutes, then rapidly heated up to 180° C. while maintaining the pressure at 100 kg/cm² for 15 minutes. The sheet obtained was cut to the size of 40×150 mm, hung in a Geer oven and tested for heat stability in air at 160° C. The degradation time was judged by looking for the time when more than 50% of pieces were discolored or deformed. The sample compounds used and the results obtained are shown in TABLE 7.

TABLE 7

| No. | SAMPLES COMPOUNDS | TIME TO BEGINNING OF DEGRADATION (hrs) |
|---|---|---|
| CONTROL | | |
| 6-1 | 4,4'-thiobis(2-t-butyl-5-methylphenol) | 65 |
| 6-2 | 2,2-bis(3,5-di-t-butyl-4-hydroxybenzyl)butanediol | 50 |
| EXAMPLE | | |
| 6-1 | No. 1 (Table-1) | 190 |
| 6-2 | No. 5 (Table-1) | 190 |
| 6-3 | No. 6 (Table-1) | 175 |
| 6-4 | No. 11 (Table-1) | 180 |
| 6-5 | No. 18 (Table-1) | 160 |
| 6-6 | No. 24 (Table-1) | 155 |
| 6-7 | No. 33 (Table-1) | 165 |
| 6-8 | No. 39 (Table-1) | 135 |

Each of the cross-linked polyethylene samples of EXAMPLES 6-1 through 6-8 stabilized according to this invention with an orthoalkylhydroxybenzylpropanediol compound had much greater heat stability than a control sample stabilized with a conventional polyhydric phenol long considered the standard antioxidant for cross-linked polyethylene.

EXAMPLES 7-1 TO 7-10

In order to examine the effects of the compounds according to this invention in ethylene-vinylacetate copolymer, samples were prepared according to the following formulation and tested for heat stability in a Geer oven at 175° C. and initial color was measured for yellowness using the Hunter color difference meter, greater numbers indicating more severe discoloration.

The results are shown in Table 8. The heat stability is expressed in minutes of heating in the oven until a red or brown discoloration was observed.

(FORMULATION)

| | |
|---|---|
| Ethylene-Vinylacetate copolymer resin | 100 parts |
| Montan Wax Ester Lubricant | 0.3 |
| Propanediol Sample Compound | 0.1 |

TABLE - 8

| No. | SAMPLE COMPOUNDS | HEAT STABILITY Min. | INITIAL COLOR |
|---|---|---|---|
| CONTROL | | | |
| 7-1 | Tris(nonylphenyl)phosphite | 80 | 0.24 |
| 7-2 | 3,3-bis(3,5-di-t-butyl-4-hydroxybenzyl)-2,4-pentanediol | 85 | 0.30 |
| EXAMPLE | | | |
| 7-1 | No. 3 (Table-1) | 135 | 0.10 |
| 7-2 | No. 4 (Table-1) | 145 | 0.10 |
| 7-3 | No. 11 (Table-1) | 140 | 0.11 |
| 7-4 | No. 16 (Table-1) | 120 | 0.12 |
| 7-5 | No. 18 (Table-1) | 130 | 0.13 |
| 7-6 | No. 23 (Table-1) | 145 | 0.11 |
| 7-7 | No. 30 (Table-1) | 140 | 0.11 |
| 7-8 | No. 31 (Table-1) | 145 | 0.09 |
| 7-9 | No. 34 (Table-1) | 115 | 0.13 |
| 7-10 | No. 38 (Table-1) | 130 | 0.12 |

Each of the ethylene-vinylacetate copolymer samples of EXAMPLES 7-1 to 7-10 stabilized according to this invention with an orthoalkylhydroxybenzylpropanediol compound had much lighter initial color and greater heat stability than a control sample stabilized with a conventional organic phosphite or with an alkylhydroxybenzylpropanediol not of this invention.

EXAMPLES 8-1 TO 8-11

In order to examine the effect of the stabilizer according to this invention on polybutene resin, a sheet of 1 mm in thickness was prepared by kneading the following formulation on a two roll mill at 140° C. for 5 minutes and then compression molding at 160° C. and 200 kg/cm² for 5 minutes. The sheet obtained was cut to the size of 40×150 mm, and tested for heat stability in individual glass cyclinders containing pure oxygen at 1 atmosphere pressure fitted with a closed end manometer and set in an oven kept at 160° C.

(FORMULATION)

| | |
|---|---|
| Un-stabilized poly-1-butylene resin | 100 parts by weight |
| Calcium stearate | 1.0 |
| Distearylthiodipropionate | 0.2 |
| Ortho-alkylhydroxybenzylpropanediol sample compound | |

The results are shown in TABLE 9. The time to beginning of oxidation degradation was read by recording the time when the pressure in the cylinder diminished rapidly.

TABLE - 9

| No. | SAMPLE COMPOUNDS | TIME TO BEGINNING OF DEGRADATION (hrs) |
|---|---|---|
| CONTROL | | |
| 8-1 | 3,3-bis(3,5-di-t-butyl-4-hydroxybenzyl)-2,4-pentanediol | 260 |
| 8-2 | Tris(3,5-di-t-butyl-4-hydroxybenzyl)isocyanurate | 330 |
| EXAMPLE | | |
| 8-1 | No. 2 (Table-1) | 530 |
| 8-2 | No. 4 (Table-1) | 570 |
| 8-3 | No. 6 (Table-1) | 560 |
| 8-4 | No. 9 (Table-1) | 490 |
| 8-5 | No. 14 (Table-1) | 510 |
| 8-6 | No. 19 (Table-1) | 470 |
| 8-7 | No. 26 (Table-1) | 480 |
| 8-8 | No. 28 (Table-1) | 510 |
| 8-9 | No. 35 (Table-1) | 500 |
| 8-10 | No. 38 (Table-1) | 520 |
| 8-11 | No. 40 (Table-1) | 500 |

Each of the poly-1-butene samples stabilized according to this invention with a stabilizer composition containing an ortho-alkylhydroxybenzylpropanediol compound had much greater heat stability than the Control sample containing a conventional phenolic antioxidant.

EXAMPLES 9-1 TO 9-7

Polycarbonate resin 100 parts by weight and sample compound 0.05 part by weight were mixed at room temperature and compression molded at 260° C. to prepare a sheet of 1.0 mm in thickness. The color of the sheet, after being heated in an air oven at 225° C. for 30 minutes, was measured and shown in TABLE 10.

TABLE - 10

| NO. | SAMPLE COMPOUNDS | COLOR OF SHEET |
|---|---|---|
| CONTROL | | |
| 9-1 | None | Dark Brown |
| 9-2 | 3,3-bis(3,5-di-t-butyl-4-hydroxybenzyl)-2,4-pentanediol | Light Brown |
| EXAMPLE | | |
| 9-1 | No. 5 (Table-1) | Light Yellow |
| 9-2 | No. 6 (Table-1) | Light Yellow |
| 9-3 | No. 14 (Table-1) | Light Yellow |
| 9-4 | No. 27 (Table-1) | Light Yellow |
| 9-5 | No. 31 (Table-1) | Light Yellow |
| 9-6 | No. 35 (Table-1) | Light Yellow |
| 9-7 | No. 37 (Table-1) | Light Yellow |

Each polycarbonate sample stabilized according to this invention was unexpectedly lighter in color than a sample without stabilizer or a sample containing an alkylhydroxybenzylpropanediol not of this invention.

EXAMPLES 10-1 TO 10-7

100 parts of nylon 66 delustered by adding 0.05% of titanium dioxide was dissolved in 90 parts of 90% formic acid, and 1.0 part of a propanediol sample compound was added and mixed completely. The solution was flowed uniformly on a glass plate, and dried in a heated air oven at 105° C. for 10 minutes to prepare a film. The color of the film, after being heated in an air oven at 225° C. for 30 minutes, was measured and shown in TABLE 11 along with the compounds present in each formulation.

TABLE - 11

| NO. | SAMPLE COMPOUNDS | COLOR OF FILM |
|---|---|---|
| CONTROL | | |
| 10-1 | None | Dark Brown |
| 10-2 | 3,3-bis(3,5-di-t-butyl-4-hydroxybenzyl)-2,4-pentanediol | Brown |
| EXAMPLE | | |
| 10-1 | No. 1 (Table-1) | Light Yellow |
| 10-2 | No. 11 (Table-1) | Light Yellow |
| 10-3 | No. 16 (Table-1) | Light Yellow |
| 10-4 | No. 25 (Table-1) | Light Yellow |
| 10-5 | No. 34 (Table-1) | Yellow |
| 10-6 | No. 36 (Table-1) | Light Yellow |
| 10-7 | No. 40 (Table-1) | Light Yellow |

Each of the nylon samples of EXAMPLES 10-1 through 10-7 stabilized with an ortho-alkylhydroxybenzylpropanediol compound of this invention gave a much lighter colored film than control samples containing instead of the substituted alkylhydroxybenzyl propanediol according to this invention propanediol not of this invention or no stabilizer.

We claim:

1. An ortho-alkylhydroxybenzylpropane-1,3-diol compound having the formula

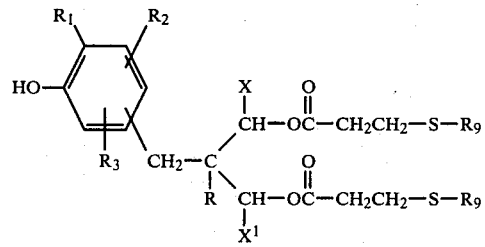

in which $R_1$ is an alkyl group having 1 to 8 carbon atoms, $R_2$ and $R_3$ are hydrogen or alkyl groups having 1 to 8 carbon atoms, R is hydrogen, an alkyl group having 1 to 8 carbon atoms, an alkenyl group having 2 to 8 carbon atoms, or an ortho-alkylhydroxybenzyl group

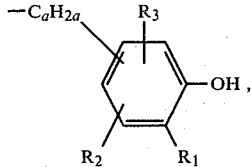

X and X' are each independently hydrogen, alkyl groups, aryl groups, aralkyl groups, or alkaryl groups having 1 to 18 carbon atoms, provided that X and X' are not simultaneously hydrogen; and $R_9$ is an alkyl group having 1 to 30 carbon atoms.

2. An ortho-alkylhydroxybenzylpropanediol compound according to claim 1 in which the orthoalkylhydroxybenzyl group is 3,5-di-t-butyl-4-hydroxybenzyl.

3. An orthoalkylhydroxybenzylpropanediol compound according to claim 1 in which the ortho-alkylhydroxybenzyl group is 4-t-butyl-4,6-dimethyl-3-hydroxybenzyl.

4. An ortho-alkylhydroxybenzylpropanediol compound according to claim 1 in which the ortho-alkylhydroxybenzyl group is 3-t-butyl-4-hydroxy-6-methylbenzyl.

5. An ortho-alkylhydroxybenzylpropanediol compound according to claim 1 in which R is hydrogen.

6. An ortho-alkylhydroxybenzylpropanediol compound according to claim 1 in which R is an ortho-alkylhydroxybenzyl group.

7. An ortho-alkylhydroxybenzylpropanediol compound according to claim 1 in which X is hydrogen and X' is an alkyl group.

8. An ortho-alkylhydroxybenzylpropanediol compound according to claim 1 in which X and X' are methyl groups.

9. An ortho-alkylhydroxybenzylpropanediol compound according to claim 1 in which $R_9$ is a n-dodecyl group.

10. An ortho-alkylhydroxybenzylpropanediol compound according claim 1 represented by the formula

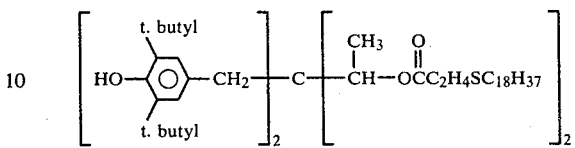

11. A stabilizer composition capable of increasing the resistance to deterioration on heating of synthetic resin, comprising an orthoalkylhydroxybenzylpropanediol compound according to claim 1 and at least one synthetic resin stabilizer selected from the group consisting of thiodipropionate esters, 1,2-epoxides, organic phosphites, polyhydric alcohols, polyhydric alcohol 3-alkylthiopropionates, ultraviolet absorbers, heavy metal deactivators, and barium, calcium, magnesium, nickel, strontium, tin, zinc salts of monocarboxylic acids having 6 to 24 carbon atoms.

12. A stabilizer composition according to claim 11 in which the synthetic resin stabilizer is a thiodiopropionate ester.

13. A stabilizer composition according to claim 11 in which the synthetic resin stabilizer is a 1,2-epoxide.

14. A stabilizer synthetic resin composition comprising a synthetic resin and 0.01 to 5% by weight of an ortho-alkylhydroxybenzylpropanediol compound according to claim 1.

15. A stabilized synthetic resin composition according to claim 14 in which the synthetic resin is a polymer of an alpha olefin having 2 to 6 carbon atoms.

16. A stabilized synthetic resin composition according to claim 14 in which the synthetic resin is a polymer of vinyl chloride.

17. A stabilized synthetic resin composition according to claim 14 in which the synthetic resin is a polymer of acrylonitrile, butadiene, and styrene.

18. A stabilized synthetic resin composition according to claim 14 in which the synthetic resin is a polymer of adipic acid and 1,6-diaminohexane.

* * * * *

UNITED STATES PATENT AND TRADEMARK OFFICE
CERTIFICATE OF CORRECTION

PATENT NO. : 4,293,472
DATED : October 6, 1981
INVENTOR(S) : Motonobu Minagawa et al It is certified that error appears in the above-identified patent and that said Letters Patent is hereby corrected as shown below:

| | |
|---|---|
| Column 1, line 30 | "eightly" should be --eighty-- |
| Column 2, line 31 | "Brown" should be --Bown-- |
| Column 3, line 65 | "Brown" should be --Bown-- |
| Column 5, line 51 | "area" should be --are a-- |
| Column 15, line 24 | "(4-t0butyl" should be --(4-t-butyl-- |
| Column 15, line 61 | "phsophite" should be --phosphite-- |
| Column 21, line 34 | "proanediol" should be --propanediol-- |
| Column 25, line 53 | "(V)" should be --2(V)-- |
| Column 34, lines 15-20 | |

"A$_2$ ; 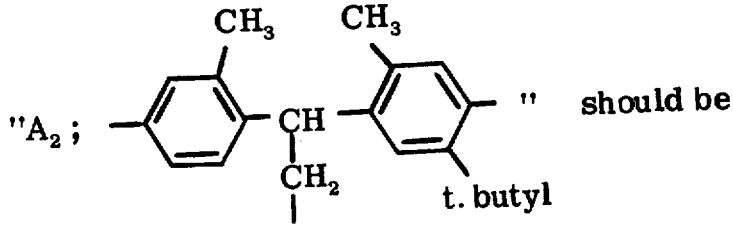 " should be

--A$_2$ ; 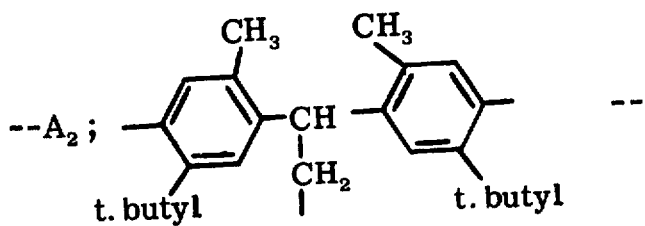 --

UNITED STATES PATENT AND TRADEMARK OFFICE
CERTIFICATE OF CORRECTION

PATENT NO. : 4,293,472
DATED : October 6, 1981
INVENTOR(S) : Motonobu Minagawa et al It is certified that error appears in the above-identified patent and that said Letters Patent is hereby corrected as shown below:

Column 30, line 1 : "buyyl" should be --butyl--
Column 42, line 62 : "4-14" should be -- 4-11--
Column 43, line 46 : "zind" should be --zinc--

Signed and Sealed this

Eighth Day of July 1986

[SEAL]

Attest:

DONALD J. QUIGG

Attesting Officer

Commissioner of Patents and Trademarks